(12) United States Patent
Kruegel et al.

(10) Patent No.: US 12,129,234 B1
(45) Date of Patent: Oct. 29, 2024

(54) CRYSTALLINE SALTS OF N-ETHYL-(5-FLUORO-1H-INDOL-3-YL)-N-METHYLETHAN-1-AMINE

(71) Applicant: Gilgamesh Pharmaceuticals, Inc., New York, NY (US)

(72) Inventors: Andrew Carry Kruegel, Millington, NJ (US); William Leong, Westfield, NJ (US); Yameng He, Halifax (CA); Lauren MacEachern, Halifax (CA)

(73) Assignee: Gilgamesh Pharmaceuticals, Inc., New York, NY (US)

( * ) Notice: Subject to any disclaimer, the term of this patent is extended or adjusted under 35 U.S.C. 154(b) by 0 days.

(21) Appl. No.: 18/368,143

(22) Filed: Sep. 14, 2023

Related U.S. Application Data

(60) Provisional application No. 63/530,671, filed on Aug. 3, 2023.

(51) Int. Cl.
*C07D 209/16* (2006.01)
(52) U.S. Cl.
CPC ........ *C07D 209/16* (2013.01); *C07B 2200/13* (2013.01)
(58) Field of Classification Search
CPC .......................... C07D 209/16; C07B 2200/13
See application file for complete search history.

(56) References Cited

U.S. PATENT DOCUMENTS

| | | | |
|---|---|---|---|
| 8,288,406 B2 | 10/2012 | Frormann et al. | |
| 11,440,879 B2 | 9/2022 | Kruegel | |
| 2012/0095217 A1 | 4/2012 | Ritter et al. | |
| 2012/0122948 A1 | 5/2012 | Soubhye et al. | |
| 2018/0021326 A1 | 1/2018 | Stamets | |
| 2018/0221396 A1 | 8/2018 | Chadeayne | |
| 2020/0030309 A1 | 1/2020 | Olson | |
| 2020/0397752 A1 | 12/2020 | Perez Castillo et al. | |
| 2022/0241243 A1 | 8/2022 | Kruegel et al. | |

FOREIGN PATENT DOCUMENTS

| | | |
|---|---|---|
| CA | 1100516 A | 5/1981 |
| CA | 1105938 A | 7/1981 |
| CN | 104276993 A | 1/2015 |
| CN | 110343050 A | 10/2019 |
| CN | 112174851 A | 1/2021 |
| CN | 113234036 A | 8/2021 |
| DE | 1668550 A1 | 7/1971 |
| DE | 2723937 A1 | 12/1977 |
| EP | 1956016 A1 | 8/2008 |
| GB | 853775 A | 11/1960 |
| KR | 20190120859 A | 10/2019 |
| WO | 2004000205 A2 | 12/2003 |
| WO | 2004000845 A1 | 12/2003 |
| WO | 2004000849 A2 | 12/2003 |
| WO | 2004043949 A1 | 5/2004 |
| WO | 2004043967 A1 | 5/2004 |
| WO | 2005063769 A1 | 7/2005 |
| WO | 2007017289 A2 | 2/2007 |
| WO | 2008071455 A1 | 6/2008 |
| WO | 2010081036 A2 | 7/2010 |
| WO | 2010136546 A1 | 12/2010 |
| WO | 2012013343 A1 | 2/2012 |
| WO | 2018064465 A1 | 4/2018 |
| WO | 2019077332 A1 | 4/2019 |
| WO | 2019081764 A1 | 5/2019 |
| WO | 2019129815 A1 | 7/2019 |
| WO | 2019160057 A1 | 8/2019 |
| WO | 2019192602 A1 | 10/2019 |
| WO | 2019220139 A1 | 11/2019 |
| WO | 2020120539 A1 | 6/2020 |
| WO | 2020181194 A1 | 9/2020 |
| WO | 2020/212948 A1 | 10/2020 |
| WO | 2021134086 A1 | 7/2021 |
| WO | 2022/047579 A1 | 3/2022 |
| WO | 2022/256554 A1 | 12/2022 |
| WO | 2023147424 A1 | 8/2023 |

OTHER PUBLICATIONS

Abolghasem Moghimi et al., "Synthesis of 2-(2-Fluorophenyl)-2-methylamino-Cyclohexanone as a New Ketamine Derivative", Syn•thetic Communications, vol. 44(14) 2021-2028 (2014). 8 pages.

Brandt Simon D. et al., "Analytical chemistry of synthetic routes to psychoactive tryptamines : Part II. Characterisation of the Speeter and Anthony synthetic route to N,N-dialkylated ttyptamines using GC-E I-IT MS, ES I-TQ-MS-MS and NMR", Analyst, vol. 130(3) 330 (2005). 15 pages.

Adamowicz Piotr et al., "Simple and rapid screening procedure for 143 new psychoactive substances by liquid chromatography•tandem mass spectrometty : Simple and rapid screening procedure for 143 new psychoactive substances", Drng Testing and Analysis, vol. 8 (7) 652-667 (2016). 16 pages.

Valentin Magne et al., "Synthesis of Spiroindolenines via Regioselec•tive Gold (I)-Catalyzed Cyclizations of N-Propargyl Tlyptamines", Advanced Synthesis and Catalysis, vol. 359 (22) 4036-4042 (2017). 7 pages.

Cozzi, Nicholas V, and Paul F Daley. "Receptor binding profiles and quantitative strncture-aflinity relationships of some 5-substituted•N,N-diallyltryptamines." Bioorganic & medicinal chemisfly letters vol. 26,3 (2016): 959-964. 6 pages.

Davidsen et al. "Ketamine analogues: Comparative toxicokinetic in vitro-in vivo extrapolation and quantification of 2-fluorodeschloroketamine in forensic blood and hair samples", J. Phann Biomed Anal. I 80: 113049 (2020). 20 pages.

(Continued)

*Primary Examiner* — Kamal A Saeed
(74) *Attorney, Agent, or Firm* — Scully, Scott, Murphy & Presser, P.C.

(57) ABSTRACT

The present disclosure relates to a crystalline N-ethyl-2-(5-fluoro-1H-indol-3-yl)-N-methylethan-1-amine salt selected from crystalline N-ethyl-2-(5-fluoro-1H-indol-3-yl)-N-methylethan-1-amine monophosphate, crystalline N-ethyl-2-(5-fluoro-1H-indol-3-yl)-N-methylethan-1-amine mono-p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate, pharmaceutical compositions comprising same, and uses thereof for treating mood disorders.

30 Claims, 15 Drawing Sheets

(56) References Cited

OTHER PUBLICATIONS

Dinger, Julia et al. "Cytochrome P450 inhibition potential of new psychoactive substances of the tryptamine class." Toxicology Letters vol. 241 (2016): 82-94. 13 pages.
Folprechtova Denisa et al., "Enantioselective potential of teicoplani••and vancomycin-based superficially porous particles-packed col•mnns for supercritical fluid chromatography", Journal of Chroma•tography A, vol. 1612 (2019). 34 pages.
Folprechtova et al. "Enantioselective potential of teicoplanin- and vancomycin-based superficially porous particles-packed columns for supercritical fluid chromatography" Journal of Chromatography A, 1612, 460687 (2020). 9 pages.
Geoffroy P. et al., "Arynic condensation of ketone enolates 19. Synthesis of polycyclic phenylethanolamines", Tetrahedron Letters, vol. 29(12) 1385-1388(1988). 4 pages.
Han Yixin et al., "Method for the Direct Enantioselective Synthesis of Chiral Primary [alpha]-Amino Ketones by Catalytic α-Amination", Organic Letters, vol. 21(1) 283-286 (2019). 4 pages.
Han, Yixin et al. "Simple Enantioselective Syntheses of (2R,6R)•Hydroxynorketamine and Related Potential Rapid-Onset Antidepressants." Organic letters vol. 19, 19 (2017): 5224-5227. 4 pages.
Hagele et al. "Enantioselective separation of Novel Psychoactive Substances using a Lux® AMP 3μm column and HPLC-UV", Journal of Pharmaceutical and Biomedical Analysis, vol. I 79 (2019). 11 pages.
Kadkhodaei Kian et al., "Separation of enantiomers of new ps••choactive substances by high-performance liquid chromatography", Journal of Separation Science, vol. 41(6) 1274-1286 (2018). 13 pages.
Krotulski et al. "Sample Mining and Data Mining: Combined Real-Time and Retrospective Approaches for the Identification of Emerging Novel Psychoactive Substances", Journal of Forensic Sciences 65(2), 550-562 (2020). 13 pages.
Lednicer D, VonVoigtlander PF, Emmert DE "4-Amino-4-arylcyclohexanones and their derivatives, a novel class of analge•sics. 1. Modification of the aryl ring" J Med Chem vol. 23(4): 424-30 (1980). 7 pages.
Mestria et al. "Method development for the identification of methoxpropamine, 2-fluoro-deschloroketamine and deschloroketamine and their main metabolites in blood and hair and forensic applic••tion", Forensic Sci Int. 323:110817 (2021). 11 pages.
Michely, Julian A et al. "Biotransformation and detectability of the new psychoactive substances N,N-diallyltryptamine (DALT) deriva•tives 5-fluoro-DALT, 7-methyl-DALT, and 5,6-methylenedioxy•DALT in urine using GC-MS, LC-MSn, and LC-HR-MS/MS." Analytical and bioanalytical chemisllyvol. 409,6 (2017): 1681-1695. 15 pages.
Michely, Julian A et al. "Dried urine spots—A novel sampling technique for comprehensive LC-MSn drng screening." Analytica chimica acta vol. 982 (2017): 112-121. 10 pages.
N-Ethyl-N-methyl-IH-indole-3-ethanamine. Accessed on SciFinder. 1 Page.
Pelchowicz, Z. et al. "N-Alkylated 5-fluorotryptamines." Journal of the Chemical Society (1961 ): 54 I 8-2 I.4 pages.
Pelletier et al. "New psychoactive substance cocktail in an intensive care intoxication case elucidated by molecular networking", Clini•cal Toxicology (2021). 5 pages.
Porpiglia, Nadia et al. "Chiral separation and determination of ketamine and norketamine in hair by capillary electrophoresis." Forensic science international vol. 266 (2016): 304-310. 7 pages.
Ryosuke et al. "Studies on generic analytical conditions of illicit drugs using supercritical fluid chromatography-mass spectrometry", Masashi Kanzei Chuo Bunsekishoho, 58, 45-79 (2019). 35 pages.
Scholten et al. "A machine-assisted approach for the preparation of follow-on pharmaceutical compound libraries" Reaction Chemistry & Engineering vol. 3(2), 210-215 (2018). 6 pages.
Shao et al. "Presence of the ketamine analog of 2-fluorodeschloroketamine residues in wastewater" Drug Test Anal. Sep. 13(9):1650-1657 (2021). 8 pages.
Soubhye, Jalal et al. "Hybrid molecules inhibiting myeloperoxidase activity and serotonin reuptake: a possible new approach of major depressive disorders with inflammatory syndrome." The Journal of pharmacy and pharmacology vol. 66,8 (2014): 1122-32. 11 pages.
Soubhye, Jalal et al. "Structure-based design, synthesis, and pha••macological evaluation of 3-(aminoalkyl)-5-fluoroindoles as myeloperoxidase inhibitors." Journal of medicinal chemislly vol. 53,24 (2010): 8747-59. 13 pages.
Stevens Cal Vin L et al., "Amino Ketone Rearrangements. VI. Synthesis of 2-Alkylamino-2-phenylcyclohexanones 1 a", Journal of Organic Chemistry, vol. 31 (8) 2593-2601 (1996). 10 pages.
Tang et al. "Emergence of new psychoactive substance 2-fluorodeschloroketamine: Toxicology and urinary analysis in a cluster of patients exposed to ketamine and multiple analogues", Forensic Sci Int. 312:110327 (2020). 27 pages.
Wang et al. "Halogen Substitution Influences Ketamine Metabolism by Cytochrome P450 2B6: In Vitro and Computational Approaches", Mol Pharm 16(2):898-906 (2019). 36 pages.
Wang, Shiyu; Li, Changxi "Synthesis of anesthetic compound 2-(o-fluorophenyl)-2-methylaminocyclohexanone hydrochloride (F-ketamine)", Beijing Daxue Xuebao, Ziran Kexueban (2), I 16-19 (1987). 4 pages.
West et al. "Early Warning System for Illicit Drng Use at Large Public Events: Trace Residue Analysis of Discarded Drng Packag•ing Samples", J Am Soc Mass Spectrom. vol. 32(10):2604-2614 (2021 ). 11 pages.
Yang Xiaoyu et al., "Direct Asymmetric Amination of [alpha]•Branched Cyclic Ketones Catalyzed by a Chiral Phosphoric Acid", Journal of the American Chemical Society, vol. 137(9) 3205-3208 (2015). 4 pages.
Kuhnz et al., "Predicting the Oral Bioavailability of 19-nortestosterone Progestins in vivo from Their Metabolic Stability in Hmnan Liver Microsomal Preparations in vitro", Drug Metabolism and Disposi•tion, vol. 26 (11) 1120-1127 (1998). 8 pages.
Lipton, Stuart A, "Failures and Successes of NMDA Receptor Antagonists: Molecular Basis for the Use of Open-channel Blockers like Memantine in the Treatment of Acute and Chronic Neurologic Insults", NeuroRx, vol. 1(1) 101-110 (2004). 10 pages.
Olivares et al., "N-methyl D-asprutate (NMDA) Receptor Antago•nists and Memantine Treatment for Alzheimer's Disease, Vascular Dementia and Parkinson's Disease", Curr Alzheimer Res, vol. 9 (6) 746-758 (2012). 25 pages.
Maurer et al., "Current Use of PSMA-PET in Prostate Cancer Management", Nat Rev Urol., vol. 13 (4) 226-235 (2016). 10 pages.
Obach, Scott R, "Prediction of Human Clearance of Twenty-nine Drugs from Hepatic Microsomal Intrinsic Clearance Data: An Exrunination of in vitro Half-life Approach and Nonspecific Binding to Microsomes", Drug Metab Dispos, vol. 27 (11) 1350-1359 (1999). 10 pages.
Hakkola, J., Hukkanen, J., Turpeinen, M et al. Inhibition and induction of CYP enzymes in humans: an update. Arch Toxicol 94, 3671-3722 (2020). 52 pages.
Setola, V., Roth, B.L. (2006). The Emergence of 5-HT2B Receptors as Targets to Avoid in Designing and Refining Phru•maceuticals. In: Roth, B.L. (eds) The Serotonin Receptors. The Receptors. Humana Press. 20 pages.
Hagele, JS, Hubner, E-M, Schmid, MG. Determination of the chiral status of different novel psychoactive substance classes by capillary electrophoresis and !3-cyclodextrin derivatives. Chirality. 2020; 32 1191-1207. 17 pages.
Kamenka Jean Marc et al., "Recherche de differences conformation•nelles et biochimiques entre phencyclidine et ketamine-[Studies on the conformational and biochemical differences between phen•cyclidine and ketamine]", European Journal of Medicinal Chemis•t.ty, vol. 20(5) 419-424 (1985). 6 pages.
U.S. Appl. No. 18/758,102, filed Jun. 28, 2024, 87 pages.
Co-pending U.S. Appl. No. 18/680,473, filed May 31, 2024.
Co-pending U.S. Appl. No. 18/368,124, filed Sep. 14, 2023.
Co-pending U.S. Appl. No. 18/368,099, filed Sep. 14, 2023.

CRYSTALLINE SALTS OF N-ETHYL-(5-FLUORO-1H-INDOL-3-YL)-N-METHYLETHAN-1-AMINE

FIELD OF THE DISCLOSURE

The present disclosure relates to novel crystalline salts, methods of preparing the same, and the use thereof to treat mood disorders in a subject.

BACKGROUND OF THE DISCLOSURE

Depression is a common psychological problem and refers to a mental state of low mood and aversion to activity. Various symptoms associated with depression include persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, and suicide attempts. The presence, severity, frequency, and duration of the above-mentioned symptoms vary on a case-by-case basis.

Approximately one third of patients with major depressive disorder (MDD) fail to achieve remission of their symptoms, even after multiple rounds of treatment with several known classes of antidepressants, including selective serotonin reuptake inhibitors (SSRIs). This high prevalence of treatment-resistant depression (TRD) makes clear the need for new, more efficacious pharmacotherapies for depression that will target new mechanisms and/or patient populations.

A class of compounds useful for treating depression and mood disorders is described in U.S. Pat. No. 11,440,879, the contents of which are incorporated by reference. It discloses, in part, compounds of the formula:

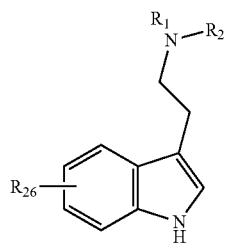

I or a pharmaceutically acceptable salt thereof, wherein
$R_1$ is optionally substituted $C_1$-$C_4$ aliphatic;
$R_2$ is optionally substituted $C_1$-$C_4$ aliphatic; and
$R_{26}$ is selected from the group consisting of hydrogen, halogen, —CN, —OH, $C_1$-$C_3$ alkoxy, $C_1$-$C_3$ haloalkyl, OAc, —OPO(OH)$_2$ and NH$_2$.

These compounds are useful for treating mood disorders, including depressive disorders. An example of one such compound within this genus is N-ethyl-(5-fluoro-1H-indol-3-yl)-N-methylethan-1-amine. However, to date, N-ethyl-2-(5-fluoro-1H-indol-3-yl)-N-methylethan-1-amine freebase has not been prepared or isolated as a crystalline solid. Although it can be used as an active pharmaceutical ingredient in a pharmaceutical composition, it is preferable to find an active ingredient of this compound that is crystalline for several reasons, including, for example, improved chemical stability, improved ability to remove impurities via recrystallization, improved solubility, improved pharmacokinetic properties, or ease of formulation in pharmaceutical compositions.

In addition, many crystalline compounds may exist in more than one crystal form, or polymorph, and relative to one another, these polymorphs exhibit different physical, chemical, and spectroscopic properties. For example, certain polymorphs of a compound may be more chemically stable, may be more readily crystallized, may be more readily soluble in particular solvents, may be more or less hygroscopic, may flow more readily, or may compress more easily than others. See, e.g., "Polymorphism in the Pharmaceutical Industry: Solid Form and Drug Development", Editor(s): Rolf Hilfiker, and Markus von Raumer, Wiley-VCH Verlag GmbH & Co. KGaA, (2018). In the case of drugs, certain solid forms may be more bioavailable than others, while others may be more stable under certain manufacturing, storage, and biological conditions. This is particularly important from a regulatory standpoint, since drugs are approved by governmental agencies, such as the U.S. Food and Drug Administration only if they meet exacting purity and characterization standards. Indeed, the regulatory approval of one polymorph of a compound, which exhibits certain solubility and physico-chemical (including spectroscopic) properties, necessarily does not imply the ready approval of other polymorphs of that same compound. Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. Modern Drug Discoveries, 2000, 53. Therefore, the discovery of new polymorphs of a drug can provide a variety of advantages.

There is a challenge in finding crystalline salts and polymorphs of pharmaceuticals. The challenge of finding crystalline salts and polymorphs of a molecule is aided by employing a number of methods known in the art. Such methods include, but are not limited to, melt recrystallization, melt cooling, solvent crystallization, desolvation, rapid evaporation, rapid cooling, slow cooling, vapor diffusion, and sublimation. Polymorphs can be detected, identified, classified, and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid-state nuclear magnetic resonance (NMR), infrared (IR) spectroscopy, Raman spectroscopy, hot-stage optical microscopy, scanning electron microscopy (SEM), electron crystallography and quantitative analysis, particle size analysis (PSA), surface area analysis, solubility, and rate of dissolution. Different physical properties of polymorphs and/or salts can affect their processing. For example, one polymorph or salt might be more likely to form solvates or might be more difficult to filter or wash free of impurities than another due to, for example, the shape or size distribution of particles of it. But, nevertheless, despite these methods, the challenge of finding the proper conditions for preparing isolating crystalline salts and/or polymorphs remains huge.

The present inventors have found such crystalline salts and means for preparing and crystallizing the same.

SUMMARY OF THE DISCLOSURE

The present disclosure relates to a crystalline N-ethyl-2-(5-fluoro-1H-indol-3-yl)-N-methylethan-1-amine salt selected from crystalline N-ethyl-2-(5-fluoro-1H-indol-3- yl)-N-methylethan-1-amine monophosphate, crystalline N-ethyl-2-(5-fluoro-1H-indol-3-yl)-N-methylethan-1-amine p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate, pharmaceutical compositions comprising same, and uses thereof for treating mood disorders. In another embodiment, the present disclosure relates to a solid substantially comprising a crystalline N-ethyl-2-(5-fluoro-1H-indol-3-yl)-N-methylethan-1-amine salt selected from crystalline N-ethyl-2-(5-fluoro-1H-indol-3-yl)-N-methylethan-1-amine monophosphate, crystalline N-ethyl-2-(5-fluoro-1H-indol-3-yl)-N-methylethan-1-amine p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate, pharmaceutical compositions comprising same, and uses thereof for treating mood disorders. In a further embodiment, the pharmaceutical composition is a solid dosage form.

BRIEF DESCRIPTION OF THE DRAWINGS

The objects, features, and advantages of the present disclosure will become apparent to one of ordinary skill in the art, in view of the following detailed description taken in combination with the attached drawings, in which.

DETAILED DESCRIPTION OF THE DISCLOSURE

Figure 1:
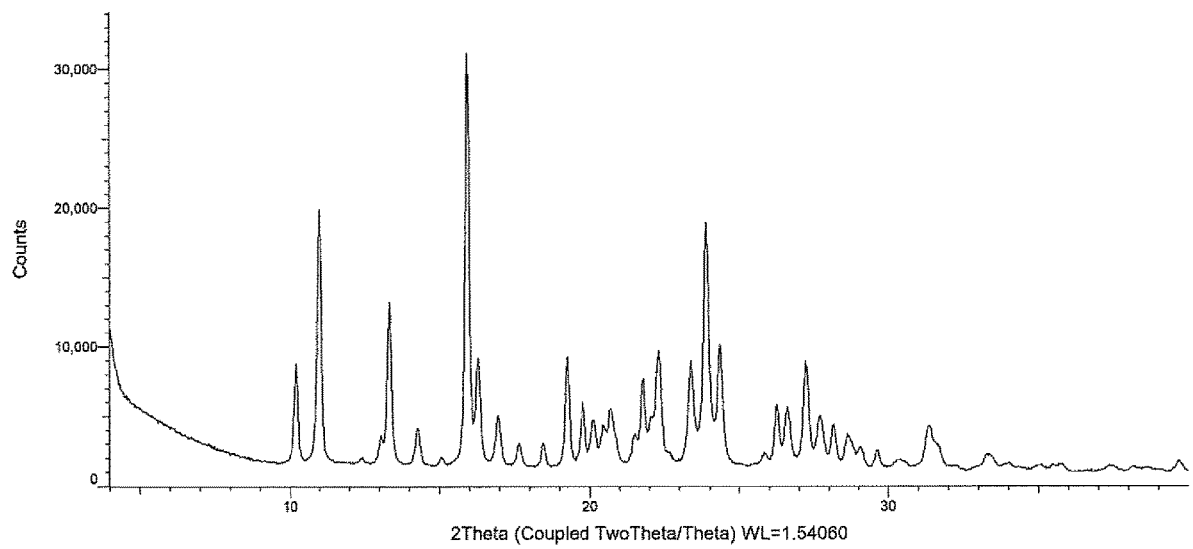
FIG. 1 depicts an XRPD diffractogram of N-ethyl-2-(5-fluoro-1H-indol-3-yl)-N-methylethan-1-amine monophosphate.

The features and other details of the disclosure will now be more particularly described. Before further description of the present disclosure, certain terms employed in the specification, examples, and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Unless indicated to the contrary, the term "free base" or "freebase" refers to N-ethyl-2-(5-fluoro-1H-indol-3-yl)-N-methylethan-1-amine in its base, unprotonated form without any counterion, which can be present as an oil or as an amorphous solid, the chemical structure of which falls within the scope of Formula I depicted hereinabove.

As used herein, the term "salt", by itself, without any free base name or acid name, unless indicated to the contrary, refers to a crystalline N-ethyl-2-(5-fluoro-1H-indol-3-yl)-N-methylethan-1-amine salt selected from crystalline N-ethyl-2-(5-fluoro-1H-indol-3-yl)-N-methylethan-1-amine monophosphate, crystalline N-ethyl-2-(5-fluoro-1H-indol-3-yl)-N-methylethan-1-amine p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate.

As defined herein, the term "solvent" refers to liquid substance or a mixture of liquid substances that is capable of dissolving another substance (solute) to form a solution, in which the solute is uniformly dispersed at the molecular or ionic size level. For purposes of this disclosure, the solvent may be a reaction solvent or a crystallizing solvent. Solvents referenced herein are inert solvents with respect to the solutes or reactants.

As defined herein, an "inert solvent" is a solvent that does not react with either the reactants or products formed in a chemical reaction.

The term "reaction solvent" or like term is a solvent in which a chemical reaction occurs. It is an inert solvent, i.e., does not react with either the free base or the acids or the product that is formed. In an embodiment, the free base and the acid are soluble therein, and the product may or may not be soluble therein. Further in an embodiment, it is a volatile solvent.

As used herein, the term "crystallizing solvent" or like term is an inert organic solvent which is used for the crystallization of a salt of the present disclosure in which the salt is poorly soluble at room temperature or low temperature, but which is more soluble when heated to the boiling point of the solvent. Ideally, the salt is nearly insoluble or sparingly soluble in the solvent at room temperature and extremely soluble at the boiling point of the solvent. The crystallizing solvent may be one solvent or a mixture of solvents. If it is a mixture of liquid solvents, they may be miscible. In an embodiment, water may be a solvent or co-solvent. The term "recrystallizing solvent", as used herein, is a crystallizing solvent, and the two terms may be used interchangeably.

The term "crystallization", as used throughout this disclosure, can refer to crystallization and/or recrystallization, depending upon the applicable circumstances relating to the preparation of the salts described herein.

The term "amorphous", as applied to a compound herein, refers to a state in which the material lacks long-range order at the molecular level, and depending upon temperature, may exhibit the properties of a solid or liquid. Typically, such materials do not give distinctive X-ray diffraction patterns.

The term "crystalline", as applied to a compound, refers to a solid phase in which the material has a regular ordered internal structure at the molecular level and gives a distinctive X-ray diffraction pattern with defined peaks. As used herein and unless otherwise indicated, the terms "polymorph" and "polymorphic form" refer to solid crystalline forms of a compound or complex. Different polymorphs of the same compound can exhibit different physical, chemical, and/or spectroscopic properties. Different physical properties include, but are not limited to, stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to a thermodynamically more stable polymorph) or both (e.g., tablets of one polymorph are more susceptible to breakdown at high humidity).

Different physical properties of polymorphs and/or salts can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art. Such methods include, but are not limited to, melt recrystallization, melt cooling, solvent crystallization, desolvation, rapid evaporation, rapid cooling, slow cooling, vapor diffusion, and sublimation. Polymorphs can be detected, identified, classified, and characterized using well-known techniques such as, but not limited to, melting point, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot-stage optical microscopy, scanning electron microscopy (SEM), electron crystallography and quantitative analysis, particle size analysis (PSA), surface area analysis, solubility, and rate of dissolution.

The term "pharmaceutically acceptable" (such as in the recitation of a pharmaceutically acceptable excipients or carriers) refers to a material that is compatible with administration to a human subject, e.g., the material does not cause an undesirable biological effect. Examples of pharmaceutically acceptable excipients are described in the "Handbook of Pharmaceutical Excipients—Ninth Edition, Edited by Paul J Sheskey, Bruno C Hancock, Gary P Moss, David J Goldfarb (2020).

The terms "treating" and "treatment" refer to ameliorating, suppressing, eradicating, reducing the severity of, decreasing the frequency of incidence of, reducing the risk of, slowing the progression of damage caused by or delaying the onset of the condition or improving the quality of life of a human patient or subject suffering from the condition.

The terms "about" or "approximately" as used herein mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range of up to 10%, a range of up to 5%, and/or a range of up to 1% of a given value. Alternatively, particularly with respect to biological systems or processes, the term can mean within an order of magnitude, e.g., within 5-fold, or within 2-fold, of a value. "About" and "approximately" are used interchangeably herein.

In embodiments, the terms "effective amount" or "therapeutically effective amount" refer to an amount of a crystalline salt described herein or pharmaceutical composition comprising same, a medicament comprising same or other material comprising same that is effective to achieve a particular pharmacological and/or physiologic effect including but not limited to reducing the frequency or severity of sadness or lethargy, depressed mood, anxious or sad feelings, diminished interest in all or nearly all activities, significant increased or decreased appetite leading to weight gain or weight loss, insomnia, irritability, fatigue, feelings of worthlessness, feelings of helplessness, inability to concentrate, and recurrent thoughts of death or suicide, or to provide a desired pharmacologic and/or physiologic effect, for example, reducing, inhibiting, or reversing one or more of the underlying pathophysiological mechanisms underlying the neurological dysfunction, modulating dopamine levels or signaling, modulating serotonin levels or signaling, modulating norepinephrine levels or signaling, modulating glutamate or GABA levels or signaling, modulating synaptic connectivity or neurogenesis in certain brain regions, or a combination thereof. The precise dosage will vary according to a variety of factors such as subject-dependent variables (e.g., age, immune system health, clinical symptoms etc.), the disease or disorder being treated, as well as the route of administration and the pharmacokinetics of the agent being administered.

"Patient" or "subject" refers to animals, and can include any mammal, such as humans, rats, mice, cats, dogs, goats, sheep, horses, monkeys, apes, rabbits, cattle, bears, and the like. The mammalian subject can be in any stage of development including adults, children, infants, and neonates.

Unless indicated to the contrary, the terms "drugs" and "medicament" are synonymous.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

When referring to a solid, the term "substantially comprising crystalline" followed by reference to a compound, such as a salt, such as N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, refers to a solid containing at least 50 wt % of the specified compound/salt in the crystalline state. It may contain other impurities. For example, the compound in an amorphous state may additionally be present, or another polymorph or salt form may be present, or other impurities may be present, but the sum of these impurities is not more than 50 wt %. In an embodiment, the solid substantially comprising crystalline may contain at least 55 wt % of the compound/salt in a crystalline state, and in another embodiment, at least 60 wt % of the compound/salt in a crystalline state; and in a further embodiment, at least 65 wt % of the compound/salt in a crystalline state; and in a still further embodiment, at least 70 wt % of the compound/salt in a crystalline state, and in another embodiment, at least 75 wt % of the compound/salt in a crystalline state, and in a still further embodiment, at least 80 wt % of the compound/salt in a crystalline state; and in a still further embodiment, at least 85 wt % of the compound/salt in a crystalline state, and in another embodiment, at least 90 wt % of the compound/salt in a crystalline state, and in a still further embodiment, at least 95 wt % of the compound/salt in a crystalline state, and in an even further embodiment, at least 99 wt % of the compound/salt in a crystalline state. Thus the amount of the crystalline salt present in the solid may be 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt % or any value therebetween. When the salts depicted are characterized by or have an XPRD pattern substantially as shown in the aforementioned figures, it is to be understood to mean that the peak pattern is basically as shown with the typical variability in peak position and intensity being taken into account. In an embodiment, at least 70% of the XPRD pattern has the peaks at the values shown with variations at 2θ angles of ±0.50, and in another embodiment, at least 75% of the XPRD pattern has the peaks at the values shown with variations at 2θ angles of ±0.50, and in another embodiment, at least 80% of the XPRD pattern has the peaks at the values shown with variations at 2θ angles of ±0.50, and in a still further embodiment, at least 85% of the XPRD pattern has the peaks at the values shown with variations at 2θ angles of ±0.50, and in still another embodiment, at least 90% of the XPRD pattern has the peaks at the values shown with variations at 2θ angles of ±0.50. As such, the peaks observed in the figures and assignments listed herein in the various tables and figures are intended to encompass variations of ±0.50 degrees 2θ and variations in relative peak intensity understood to be acceptable by one skilled in the art. When listing the peaks for the XRPDs, it is to be understood that each of the values listed are ±0.50° 2θ, even when ±0.50° 2θ is not recited in the listing. Further, when a listing of the chain of peaks is provided with ±0.50° 2θ at the end of the chain, for purposes of this disclosure, each value in the chain of peaks is modified by the variation ±0.50° 2θ.

As used herein when referring to the spectra or data presented in graphical form (e.g., XRPD, DSC, IR, Raman, and NMR spectra), and unless otherwise indicated, the term "peak" refers to a peak or other special feature that one skilled in the art would recognize as not attributable to background noise.

When listing the peaks for the XRPDs, it is to be understood that each of the values listed are varied by ±0.50° 2θ (or ±0.1,±0.2, ±0.3 and ±0.4 degrees 2θ), even when ±0.50° 2θ (±0.1,±0.2, ±0.3 and ±0.4 degrees 2θ). is not recited in the listing. Further, when a listing of the chain of peaks is provided with ±0.50° 2θ at the end of the chain, for purposes of this disclosure, each value in the chain of peaks is modified by the variation ±0.50° 2θ (±0.1,±0.2, ±0.3 and ±0.4 degrees 2θ).

It should be understood, however, that relative intensities and assignment of the peaks of the salts depicted in these figures can vary depending on a number of factors, including, without limitation, sample preparation, mounting, and the instrument and analytical procedure and settings used to obtain the spectrum. As such, the peaks observed in the figures and assignments listed herein in the various tables and figures are intended to encompass variations of plus or minus 0.5 degrees 2θ. However, it is to be understood that the tables and figures also encompass variations of 0.1, 0.2, 0.3 and 0.4 degrees 2θ.

In summary, with respect to the term "substantially as shown" regarding XRPD means that variability typical for a particular method is taken into account. For example, with reference to X-ray diffraction peak positions, the term "substantially as shown" refers to that typical variability in peak position and intensity being taken into account. One skilled in the art will appreciate that the peak positions (2θ) will show some variability, typically ±0.5°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

With respect to the term substantially as shown with respect to DSC, the variability of values are taken into account. The shape of the thermogram is as shown and but the values of the peaks may vary and the value of the peaks are to be understood to be about the values shown.

As used herein, when reference is made to the spectra or data presented in graphical form (e.g., XRPD, and NMR spectra), and unless otherwise indicated, the term "peak" refers to a peak or other special feature that one skilled in the art would recognize as not attributable to background noise.

Also, the use of "a" or "an" are employed to describe elements and components described herein. This is done merely for convenience and to give a general sense of the scope of the invention. This description should be read to include one or at least one.

Moreover, the singular also includes the plural and vice versa unless it is obvious that it is meant otherwise.

Further, unless expressly stated to the contrary, "or" refers to an inclusive "or" and not to an exclusive "or." For example, a condition A or B is satisfied by any one of the following: A is true (or present), and B is false (or not present), A is false (or not present), and B is true (or present), and both A and B are true (or present).

Moreover, the term "and/or" is synonymous with the term "or", as used herein.

When a range of values is expressed, an embodiment includes the endpoint of the ranges and all the points therebetween. For example, a range of 6 to 9, includes the value 6 and 9 and all values therebetween. Similarly, when values are expressed as approximations, by use of the antecedent "about," it will be understood that the values range from about the two endpoints, where "about" is defined as herein described. All ranges are inclusive and combinable. Further, reference to values stated in ranges includes each and every value within that range.

Unless otherwise defined, all technical and scientific terms used herein have the same meaning as commonly understood by one of ordinary skill in the art to which this invention belongs.

Although methods and materials similar or equivalent to those described herein can be used in the practice or testing of embodiments of the present invention, suitable methods and materials are described below. All publication, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Unless indicated to the contrary, all percentages are by weight.

The present disclosure relates, in part, to a crystalline salt of N-ethyl-2-(5-fluoro-1H-indol-3-yl)-N-methylethan-1-amine selected from crystalline N-ethyl-2-(5-fluoro-1H-indol-3-yl)-N-methylethan-1-amine monophosphate, crystalline N-ethyl-2-(5-fluoro-1H-indol-3-yl)-N-methylethan-1-amine p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate, methods of preparing them, and uses thereof for treating mood disorders.

The present disclosure not only describes the aforementioned crystalline salts and also provides a means for making and using these aforementioned crystalline salts.

In many cases, the salts of the free base of N-ethyl-2-(5-fluoro-1H-indol-3-yl)-N-methylethan-1-amine are isolated or formed in situ from the reaction of the free base with the appropriate acid. For example, N-ethyl-2-(5-fluoro-1H-indol-3-yl)-N-methylethan-1-amine monophosphate is prepared from the reaction of the free base and phosphoric acid; N-ethyl-2-(5-fluoro-1H-indol-3-yl)-N-methylethan-1-amine p-tosylate is prepared from the reaction of the free base and para-toluenesulfonic acid; N-ethyl-2-(5-fluoro-1H-indol-3-yl)-N-methylethan-1-amine hemimalate is prepared from the reaction of the free base and malic acid; and N-ethyl-2-(5-fluoro-1H-indol-3-yl)-N-methylethan-1-amine monosuccinate is prepared from the reaction of the free base and succinic acid. Moreover, in many cases, the reaction of the acid with the free base is conducted in a solvent. In an embodiment, the free base is soluble in the solvent, but the product salt is insoluble in the solvent at room temperature. In a further embodiment, the reaction is conducted in a crystallizing solvent. In an embodiment, the solvent/cosolvent has a boiling point below the melting point of the salt that is crystallized.

The free base of N-ethyl-2-(5-fluoro-1H-indol-3-yl)-N-methylethan-1-amine is prepared as described in U.S. Pat. No. 11,440,879, the contents of which are incorporated by reference. Moreover, it can also be prepared from any of the salts in Examples 1-3 herein or from the salts described in co-pending application entitled "CRYSTALLINE HYDROCHLORIDE SALTS OF N-ETHYL-(5-FLUORO-1-H-INDOL-3-YL)-N-METHYL ETHAN-1-AMINE" (SSMP DOCKET: 42180) and "CRYSTALLINE FUMARATE SALTS OF N-ETHYL-(5-FLUORO-1-H-INDOL-3-YL)-N-METHYL ETHAN-1-AMINE" (SSMP Docket: 42468), the contents of all of which are incorporated by reference. The free base is prepared by reacting the salt with base, typically in a suitable solvent system, by techniques well known in the art. For example, N-ethyl-2-(5-fluoro-1H-indol-3-yl)-N-methylethan-1-amine free base is prepared by reacting any one of the salts of N-ethyl-2-(5-fluoro-1H-indol-3-yl)-N-methylethan-1-amine with a suitable base, such as NaOH, KOH, ammonia, NaHCO$_3$, Na$_2$CO$_3$, triethylamine, pyridine, and the like. Typically, the basification reaction is conducted in an organic solvent that is immiscible with water. Subsequent to the reaction of the salt and base to form the free base of N-ethyl-2-(5-fluoro-1H-indol-3-yl)-N-methylethan-1-amine, the organic phase is washed with water or an aqueous phase to remove inorganic salts formed in the reaction, residual N-ethyl-2-(5-fluoro-1H-indol-3-yl)-N-methylethan-1-amine salt, or other impurities, while leaving the free base of N-ethyl-2-(5-fluoro-1H-indol-3-yl)-N-methylethan-1-amine in the organic layer. The organic solvent is then evaporated by heating or under reduced pressure to provide the free base of N-ethyl-2-(5-fluoro-1H-indol-3-yl)-N-methylethan-1-amine as an oil or amorphous solid.

In an embodiment, the crystalline salts described herein are anhydrous, that is, they contain less than 5% water by weight, and in an embodiment, contain less than 4% water, and in another embodiment, contain less than 3% water, and in another embodiment, contain less than 2% water, and in another embodiment, contain less than 1% water.

In an embodiment, the solid described herein may be substantially pure. In another embodiment, it may be polymorphically pure, and in a still further embodiment, it may be both substantially pure and polymorphically pure. In another embodiment, the solid is anhydrous and substantially pure, and in another embodiment, is polymorphically pure and is anhydrous, and in a still further embodiment, is substantially pure, polymorphically pure, and is anhydrous.

EXEMPLIFICATION

The various salts described herein are prepared as described hereinbelow, the techniques of which are known to one of ordinary skill in the art. These examples are illustrative of the techniques for preparing the crystalline N-ethyl-2-(5-fluoro-1H-indol-3-yl)-N-methylethan-1-amine salts. The abbreviations used in the specification are indicated below:

DSC—Differential Scanning calorimetry
NMR—Nuclear Magnetic Resonance
XRPD—X-ray Powder Diffraction.
ACN—acetonitrile
DCM—dichloromethane
ETOAc—ethyl acetate
MEK—methyl ethyl ketone
MtBE—tert-butyl methyl ether
MIBK—methyl isobutyl ketone
IPA—isopropyl alcohol
DW—distilled water
iPrOAc—isopropyl acetate
DMSO—dimethyl sulfoxide
THF—tetrahydrofuran
TSA—p-toluenesulfonic acid
Volume—typically 1 ml per gram of compound or 1 microliter per mg of compound In the examples below, various types of data are obtained using various machines. For example, XRPD was performed using a Rigaku MiniFlex 600 in reflection mode (i.e. Bragg-Brentano geometry). Samples were prepared on Si zero-return wafers. The parameters for XRPD analysis used are listed below:

| Parameter | Regular scan |
|---|---|
| X-ray wavelength | Cu Kα1, 1.540598 Å |
| X-ray tube setting | 40 kV, 15 mA |
| Slit condition | 1.25° div., Ni kβ filter, 0.3 mm rec. |
| Scan mode | Continuous |
| Scan range (°2θ) | 4-30 |
| Step size (°2θ) | 0.05 |
| Scan speed (°/min) | 5 |
| Spin | No |

Alternatively, XRPD was performed using a Bruker D8 Advance equipped with LYNXEYE detector in reflection mode (i.e. Bragg-Brentano geometry). Samples were prepared on Si zero-return wafers. The parameters for XRPD methods used are listed below:

| Parameter | Regular scan | High resolution scan |
|---|---|---|
| X-ray wavelength | Cu Kα1, 1.540598 Å | Cu Kα1, 1.540598 Å |
| X-ray tube setting | 40 kV, 40 mA | 40 kV, 40 mA |
| Slit condition | 0.6 mm div. + 2.5° soller | 0.6 mm div. + 2.5° soller |
| Scan mode | Step | Step |
| Scan range (°2θ) | 4-30 | 4-40 |
| Step size (°2θ) | 0.03 | 0.02 |
| Dwell time (s/step) | 0.23 | 0.9 |
| Spin | Yes (0.5 Hz) | Yes (0.5 Hz) |

$^1$H NMR was performed on Bruker Avance 300 MHz or 500 MHz spectrometers. Solids were dissolved in 0.75 mL deuterated solvent in a 4 mL vial, transferred to an NMR tube (Wilmad 5 mm thin wall 8$^2$ 200 MHz, 506-PP-8) and analyzed according to the following parameters:

| Parameters - Bruker Avance 300 | |
|---|---|
| Instrument | Bruker Avance 300 MHz spectrometer |
| Temperature | 300 K |
| Probe | 5 mm PABBO BB-1H/DZ-GRD Z104275/0170 |
| Number of scans | 16 |
| Relaxation delay | 1.000 s |
| Pulse width | 14.2500 μs |
| Acquisition time | 2.9999 s |
| Spectrometer frequency | 300.15 MHz |
| Nucleus | $^1$H |

| Parameters - Bruker Avance 500 | |
|---|---|
| Instrument | Bruker Avance 500 MHz spectrometer |
| Temperature | 300 K |
| Probe | 5 mm PABBO BB-1H/DZ-GRD Z113652/0159 |
| Number of scans | 32 |
| Relaxation delay | 1.000 s |
| Pulse width | 14.0000 μs |
| Acquisition time | 3.2506 s |
| Spectrometer frequency | 500.13 MHz |
| Nucleus | $^1$H |

DSC was performed using a TA Discovery DSC. The sample (1-5 mg) was weighed directly in a 40 μL hermetic aluminum pan with a pinhole and analyzed according to the parameters below:

| Parameters | |
|---|---|
| Method | Ramp |
| Sample size | 1-5 mg |
| Heating rate | 10.0° C./min |
| Temperature range | 30 to 300 ° C. |
| Method gas | N$_2$ at 50.00 mL/min |

DSC is an analytical technique that measures the amount of heat absorbed or released while heating or cooling a sample over a range of temperature. Not only does it measure the thermal properties of a material, but it also measures the temperature at which phase transitions occur, including glass transition temperatures, as well as exothermic events, at which crystallization occurs, and endothermic events, at which melting occurs. Obviously, the graph that is recorded by this instrument is affected by the purity of the sample. Pure compounds have sharp melts, usually a 1-2 degree C. range, while impure compounds melt earlier, usually 1-3 degree lower than pure compounds and have broader melt ranges, e.g., 3-5 degrees C. The graph produced may have maximum peaks and minimum peaks. The maximum peak is an exothermic event where crystallization occurs, and a minimum peak is an endothermic event, where melting occurs.

A. Screening Experiments

A number of methods known in the art exist for discovering salts of a molecule and polymorphs of a molecule. Such methods include, but are not limited to, melt recrystallization, melt cooling, solvent crystallization, desolvation, rapid evaporation, rapid cooling, slow cooling, vapor diffusion and sublimation.

The table below summarizes selected data from salt and polymorph screening experiments following a solvent crystallization method. These experiments were conducted using N-ethyl-2-(5-fluoro-1H-indol-3-yl)-N-methylethan-1-amine freebase, the selected acid, and the solvent in the volumes indicated in the table. The mixtures were agitated until solids were observed. The solids were collected by filtration and analyzed using XRPD in their wet cake state and, in some instances, in their dry cake state after being in a vacuum oven for at least 3 hours.

Figure 4:
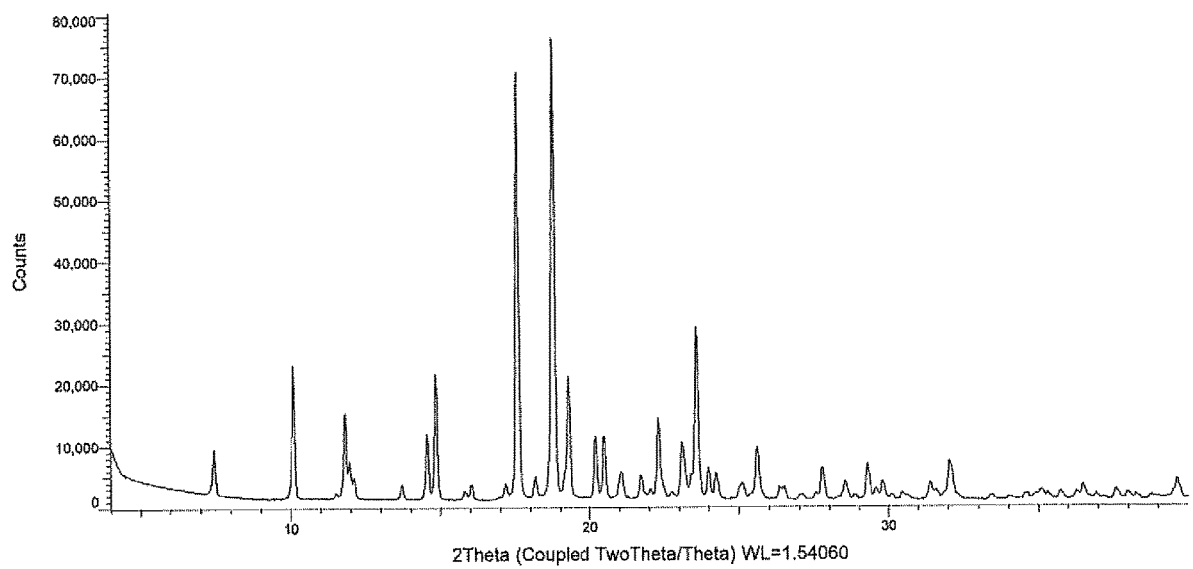
FIG. 4 depicts an XRPD diffractogram of N-ethyl-2-(5-fluoro-1H-indol-3-yl)-N-methylethan-1-amine p-tosylate.
Figure 7:
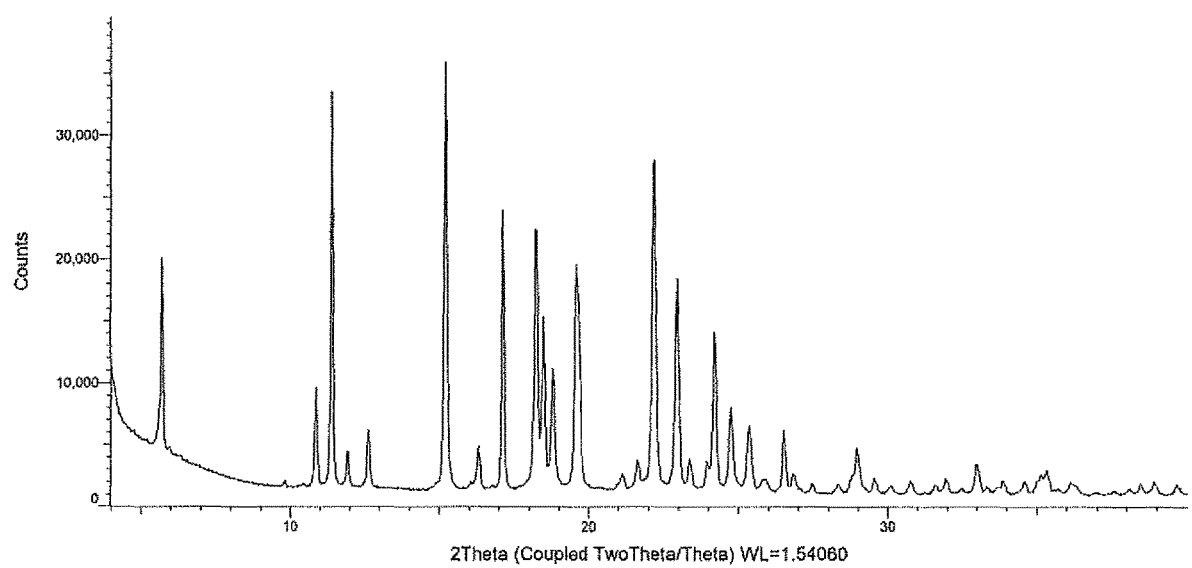
FIG. 7 depicts an XRPD diffractogram of N-ethyl-2-(5-fluoro-1H-indol-3-yl)-N-methylethan-1-amine hemimalate.
Figure 10:
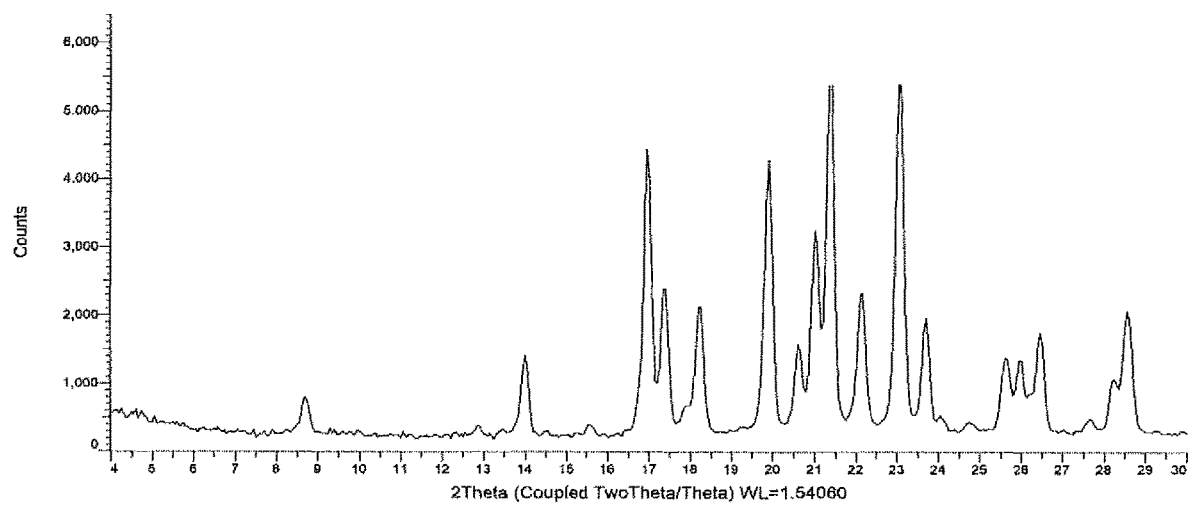
FIG. 10 depicts an XRPD diffractogram of N-ethyl-2-(5-fluoro-1H-indol-3-yl)-N-methylethan-1-amine monosuccinate.

| Acid | Solvent | XRPD pattern of wet cake | XRPD pattern of dry cake |
|---|---|---|---|
| Phosphoric acid (1.1 eq.) | 20 vol of IPA:water (9:1) | FIG. 1 | FIG. 1 |
|  | 20 vol of IPA | FIG. 1 | — |
|  | 20 vol of Acetone | FIG. 1 | — |
| p-Toluene-sulfonic acid (1.1 eq.) | 10 vol of EtOH:MtBE (1:1) | FIG. 4 | — |
|  | 10 vol of EtOAc | FIG. 4 | FIG. 4 |
|  | 10 vol of MIBK | FIG. 4 | — |
| L-Malic acid (0.55 eq.) | 20 vol of IPA | FIG. 7 | FIG. 7 |
| Succinic acid (1.1 eq.) | 20 vol of IPA | FIG. 10 | FIG. 10 |
|  | 20 vol of Acetone followed by 40 vol of Heptane | FIG. 10 | — |

The preparation of the various salts, N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate and accompanying physical data are described below.

B. N-ethyl-2-(5-fluoro-1H-indol-3-yl)-N-methyl-ethan-1-amine monophosphate

N-ethyl-2-(5-fluoro-1H-indol-3-yl)-N-methylethan-1-amine monophosphate is prepared by reacting N-ethyl-2-(5-fluoro-1H-indol-3-yl)-N-methylethan-1-amine freebase with phosphoric acid under conditions effective to form N-ethyl-2-(5-fluoro-1H-indol-3-yl)-N-methylethan-1-amine monophosphate. For example, its preparation is conducted in a polar solvent comprising isopropyl alcohol, acetone, or a solvent mixture of isopropyl alcohol and water in a ratio of about 9:1 (v/v). In an embodiment, the solvent mixture comprising isopropyl alcohol and water may be present in a ratio ranging from about 70:30 to about 99:1 (v/v), such as about 70:30, about 75:25, about 80:20, about 85:15, about 90:10, about 95:5, about 96:4, about 97:3, about 98:2, or about 99:1 (v/v) and any value therebetween. Regardless of which of the aforementioned solvent systems is used, the reaction is conducted under effective conditions. For example, the reaction is heated slightly with stirring, at effective temperatures to form the N-ethyl-2-(5-fluoro-1H-indol-3-yl)-N-methylethan-1-amine monophosphate and keep it fully or partially dissolved. In an embodiment, for example, the reaction may be heated at a temperature ranging from about 30° C. to about 60° C., such as about 45° C. with stirring to form a gum comprising N-ethyl-2-(5-fluoro-1H-indol-3-yl)-N-methylethan-1-amine monophosphate. When a gum is formed, it is sonicated to form a flowable slurry therefrom comprising N-ethyl-2-(5-fluoro-1H-indol-3-yl)-N-methylethan-1-amine monophosphate. The slurry is cooled to about room temperature, and the N-ethyl-2-(5-fluoro-1H-indol-3-yl)-N-methylethan-1-amine monophosphate is crystallized from said slurry, for example by seeding, scratching, or aging, to form a crystalline solid substantially comprising N-ethyl-2-(5-fluoro-1H-indol-3-yl)-N-methylethan-1-amine monophosphate.

The following example is further illustrative of the subject matter described in this disclosure.

EXAMPLE 1: Preparation of N-ethyl-2-(5-fluoro-1H-indol-3-yl)-N-methylethan-1-amine monophosphate Freebase N-ethyl-2-(5-fluoro-1H-indol-3-yl)-N-methylethan-1-amine in 10 volumes of IPA was treated with about 0.4 mole equivalents of phosphoric acid that was added dropwise then stirred for 25 min. Some off-white gum formed at the bottom of the vial. To break up the gum, the vial was sonicated for 5 min when a white slurry was observed. The slurry was seeded with a micro-spatula of crystals isolated from previous screening experiments to produce a solid product. Another 0.7 mole equivalents of phosphoric acid was added dropwise and a gum formation was observed. The vial was sonicated until a flowable, white slurry was obtained. The slurry was stirred at 45° C. for another 2 hours, then cooled to room temperature and allowed to stir for 4 hours. The slurry was filtered and the filter cake was washed three times with 1 vol. of IPA. The resulting solid was dried overnight under vacuum at 50° C. The dry solid that was recovered was crystalline N-ethyl-2-(5-fluoro-1H-indol-3-yl)-N-methylethan-1-amine monophosphate.

The product was analyzed by XPRD according to the parameters described hereinabove. The XRPD diffractogram of N-ethyl-2-(5-fluoro-1H-indol-3-yl)-N-methylethan-1-amine monophosphate is depicted in FIG. 1. The peak values and intensity are provided hereinbelow in the following table:

| Angle (°2θ) | d-spacing (Å) | Relative intensity |
|---|---|---|
| 10.20 | 8.66 | 23 |
| 10.99 | 8.05 | 62 |
| 12.42 | 7.12 | 1 |
| 13.06 | 6.77 | 6 |
| 13.34 | 6.63 | 38 |
| 14.29 | 6.19 | 8 |
| 15.08 | 5.87 | 2 |
| 15.92 | 5.56 | 100 |
| 16.28 | 5.44 | 24 |
| 16.94 | 5.23 | 11 |
| 17.64 | 5.02 | 4 |
| 18.44 | 4.81 | 4 |
| 19.24 | 4.61 | 24 |
| 19.75 | 4.49 | 14 |
| 20.11 | 4.41 | 10 |
| 20.46 | 4.34 | 9 |
| 20.68 | 4.29 | 12 |
| 21.51 | 4.13 | 6 |
| 21.78 | 4.08 | 20 |
| 22.06 | 4.03 | 11 |
| 22.30 | 3.98 | 27 |
| 22.67 | 3.92 | 2 |
| 23.38 | 3.80 | 25 |
| 23.88 | 3.72 | 58 |
| 24.34 | 3.65 | 29 |
| 25.82 | 3.45 | 2 |
| 26.24 | 3.39 | 14 |
| 26.60 | 3.35 | 14 |
| 27.22 | 3.27 | 24 |
| 27.70 | 3.22 | 12 |
| 28.14 | 3.17 | 9 |
| 28.63 | 3.12 | 7 |
| 29.05 | 3.07 | 3 |
| 29.64 | 3.01 | 3 |
| 30.39 | 2.94 | 1 |
| 31.38 | 2.85 | 10 |
| 31.64 | 2.83 | 6 |
| 33.36 | 2.68 | 3 |
| 33.97 | 2.64 | 1 |
| 35.03 | 2.56 | 1 |
| 35.47 | 2.53 | 1 |
| 35.72 | 2.51 | 1 |
| 37.43 | 2.40 | 1 |
| 38.19 | 2.35 | 1 |
| 38.60 | 2.33 | 1 |
| 39.68 | 2.27 | 2 |

Note. Cut-off for relative intensity was 1.

In an embodiment, the X-ray powder diffraction pattern which was measured using Cu K-alpha radiation comprises peaks at 10.99±0.50 degrees, 15.92±0.50 degrees, and 23.88±0.50 degrees 2θ. In another embodiment, the X-ray powder diffraction pattern which was measured using Cu K-alpha radiation, comprises peaks at 10.99±0.50 degrees, 13.34±0.50 degrees, 15.92±0.50 degrees, 23.88±0.50 degrees, 24.34±0.50 degrees 2θ. In another embodiment, the X-ray powder diffraction pattern which was measured using Cu K-alpha radiation, comprises peaks at 10.99±0.50 degrees, 13.34±0.50 degrees, 15.92±0.50 degrees, 16.28±0.50 degrees, 19.24±0.50 degrees, 22.30±0.20 degrees, 23.38±0.50 degrees, 23.88±0.50 degrees, 24.34±0.50 degrees, and 27.22±0.50 degrees 2θ. In a further embodiment, the X-ray powder diffraction pattern which was measured using Cu K-alpha radiation, comprises peaks at 10.20±0.50, 10.99±0.50, 12.42±0.50, 13.06±0.50, 13.34±0.50, 14.29±0.50, 15.08±0.50, 15.92±0.50, 16.28±0.50, 16.94±0.50, 17.64±0.50, 18.44±0.50, 19.24±0.50, 19.75±0.50, 20.11±0.50, 20.46±0.50, 20.68±0.50, 21.51±0.50, 21.78±0.50, 22.06±0.50, 22.30±0.50, 22.67±0.50, 23.38±0.50, 23.88±0.50, 24.34±0.50, 25.82±0.50, 26.24±0.50, 26.60±0.50, 27.22±0.50, 27.70±0.50, 28.14±0.50, 28.63±0.50, 29.05±0.50, 29.64±0.50, 30.39±0.50, 31.38±0.50, 31.64±0.50, 33.36±0.50, 33.97±0.50, 35.03±0.50, 35.47±0.50, 35.72±0.50, 37.43±0.50, 38.19±0.50, 38.60±0.50, 39.68±0.50 degrees 2θ.

Figure 2:
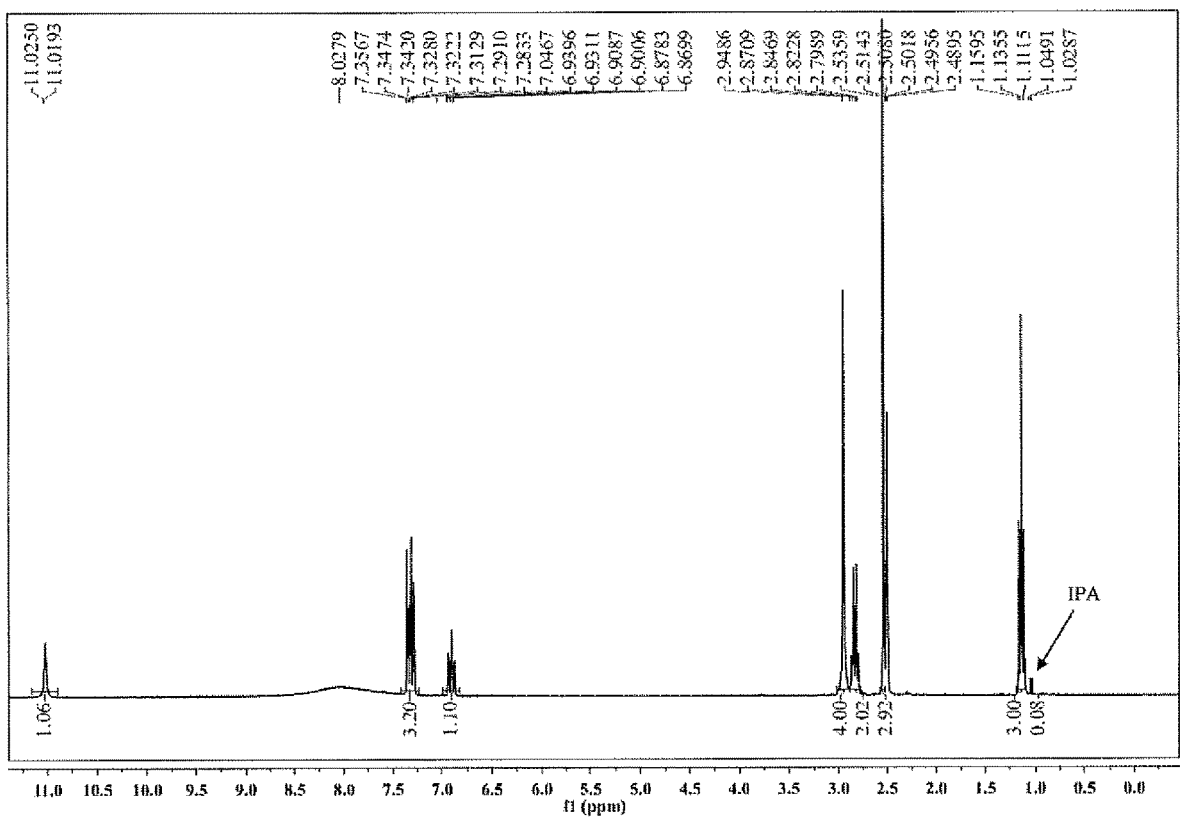
FIG. 2 depicts an $^1$H NMR spectrum (300 MHz, DMSO-d6) of N-ethyl-2-(5-fluoro-1H-indol-3-yl)-N-methylethan-1-amine monophosphate.

An $^1$H NMR was also recorded of the monophosphate product according to the parameters described hereinabove, with the result depicted in FIG. 2. A DSC thermogram of the monophosphate product was collected according to the parameters described hereinabove, with the result depicted in FIG. 3. The DSC thermogram had a sharp temperature peak at about 206° C.

B. N-ethyl-2-(5-fluoro-1H-indol-3-yl)-N-methyl-ethan-1-amine p-tosylate

N-ethyl-2-(5-fluoro-1H-indol-3-yl)-N-methylethan-1-amine p-tosylate is prepared by reacting N-ethyl-2-(5-fluoro-1H-indol-3-yl)-N-methylethan-1-amine freebase with p-toluenesulfonic acid under conditions effective to form N-ethyl-2-(5-fluoro-1H-indol-3-yl)-N-methylethan-1-amine p-tosylate. For example, its preparation is conducted in a first polar solvent, for example, comprising ethyl acetate, acetone, or a mixture comprising ethanol and MtBe in a ratio ranging from about 30:70 to about 70:30 (v/v), such as 1:1 ratio (v/v). The solvent mixture comprising ethanol and MtBe may be present in a ratio ranging from about 70:30 to about 30:70 (v/v), such as about 70:30, about 65:35, about 60:40, about 55:45, about 50:50, about 45:55, about 40:60, about 35:65, or about 30:70 (v/v), and any ratio therebetween. Regardless of which of the aforementioned solvent systems is used, the reaction is conducted under effective conditions. For example, the reaction is heated slightly with stirring, at effective temperatures to form the N-ethyl-2-(5-fluoro-1H-indol-3-yl)-N-methylethan-1-amine p-tosylate and keep it fully or partially dissolved. For example, the reaction may be heated at a temperature ranging from about 30° C. to about 60° C., such as about 45° C., with stirring to form a slurry comprising N-ethyl-2-(5-fluoro-1H-indol-3-yl)-N-methylethan-1-amine p-tosylate. The slurry is cooled to about room temperature, and the N-ethyl-2-(5-fluoro-1H-indol-3-yl)-N-methylethan-1-amine p-tosylate is crystallized from said slurry, for example, by seeding, scratching, or aging, to form a crystalline solid substantially comprising N-ethyl-2-(5-fluoro-1H-indol-3-yl)-N-methylethan-1-amine p-tosylate.

The following example is further illustrative of the subject matter in the present disclosure:

EXAMPLE 2: Preparation of N-ethyl-2-(5-fluoro-1H-indol-3-yl)-N-methylethan-1-amine p-tosylate A mole equivalent of freebase was stirred with 1.1 mole equivalent of para-toluenesulfonic acid crystals in 10 volumes of EtOAc solvent. The mixture was stirred at 45° C. until a white slurry was observed. The slurry was seeded with a micro-spatula tip of solid product isolated from a previous sample that is prepared from a screening experiment, and stirred for 4 hours at room temperature. The slurry was filtered and washed with EtOAc. The resulting white solid was dried for ~12 h under vacuum. Crystalline N-ethyl-2-(5-fluoro-1H-indol-3-yl)-N-methylethan-1-amine p-tosylate was collected and analyzed by XRPD according to the parameters described hereinabove. The XRPD diffractogram of N-ethyl-2-(5-fluoro-1H-indol-3-yl)-N-methylethan-1-amine p-tosylate is depicted in FIG. 4. The peak values and intensity are provided hereinbelow in the following table:

| Angle (°2θ) | d-spacing (Å) | Relative intensity |
|---|---|---|
| 7.44 | 11.87 | 9 |
| 10.09 | 8.76 | 28 |
| 11.52 | 7.67 | 1 |
| 11.81 | 7.48 | 18 |
| 11.96 | 7.39 | 8 |
| 12.11 | 7.30 | 4 |
| 13.70 | 6.46 | 2 |
| 14.56 | 6.08 | 13 |
| 14.85 | 5.96 | 26 |
| 15.81 | 5.60 | 1 |
| 16.03 | 5.52 | 2 |
| 17.17 | 5.16 | 2 |
| 17.57 | 5.04 | 91 |
| 18.16 | 4.88 | 3 |
| 18.77 | 4.73 | 100 |
| 19.27 | 4.60 | 25 |
| 20.19 | 4.39 | 13 |
| 20.48 | 4.33 | 13 |
| 21.07 | 4.21 | 5 |
| 21.73 | 4.09 | 4 |
| 22.06 | 4.03 | 1 |
| 22.32 | 3.98 | 17 |
| 22.77 | 3.90 | 1 |
| 23.11 | 3.85 | 11 |
| 23.41 | 3.80 | 5 |
| 23.59 | 3.77 | 35 |
| 23.98 | 3.71 | 5 |
| 24.25 | 3.67 | 4 |
| 25.10 | 3.54 | 2 |
| 25.59 | 3.48 | 9 |
| 26.33 | 3.38 | 2 |
| 26.47 | 3.36 | 2 |
| 27.77 | 3.21 | 6 |
| 28.52 | 3.13 | 3 |
| 29.27 | 3.05 | 6 |
| 29.56 | 3.02 | 2 |
| 29.78 | 3.00 | 3 |
| 31.39 | 2.85 | 3 |
| 31.59 | 2.83 | 2 |
| 32.04 | 2.79 | 7 |
| 34.62 | 2.59 | 1 |
| 34.92 | 2.57 | 1 |
| 35.09 | 2.56 | 2 |
| 35.31 | 2.54 | 1 |
| 35.74 | 2.51 | 1 |
| 36.27 | 2.47 | 2 |
| 36.48 | 2.46 | 3 |
| 36.92 | 2.43 | 1 |
| 37.61 | 2.39 | 2 |
| 37.99 | 2.37 | 1 |
| 38.26 | 2.35 | 1 |
| 39.67 | 2.27 | 4 |

Note. Cut-off for relative intensity was 1.

Figure 5:
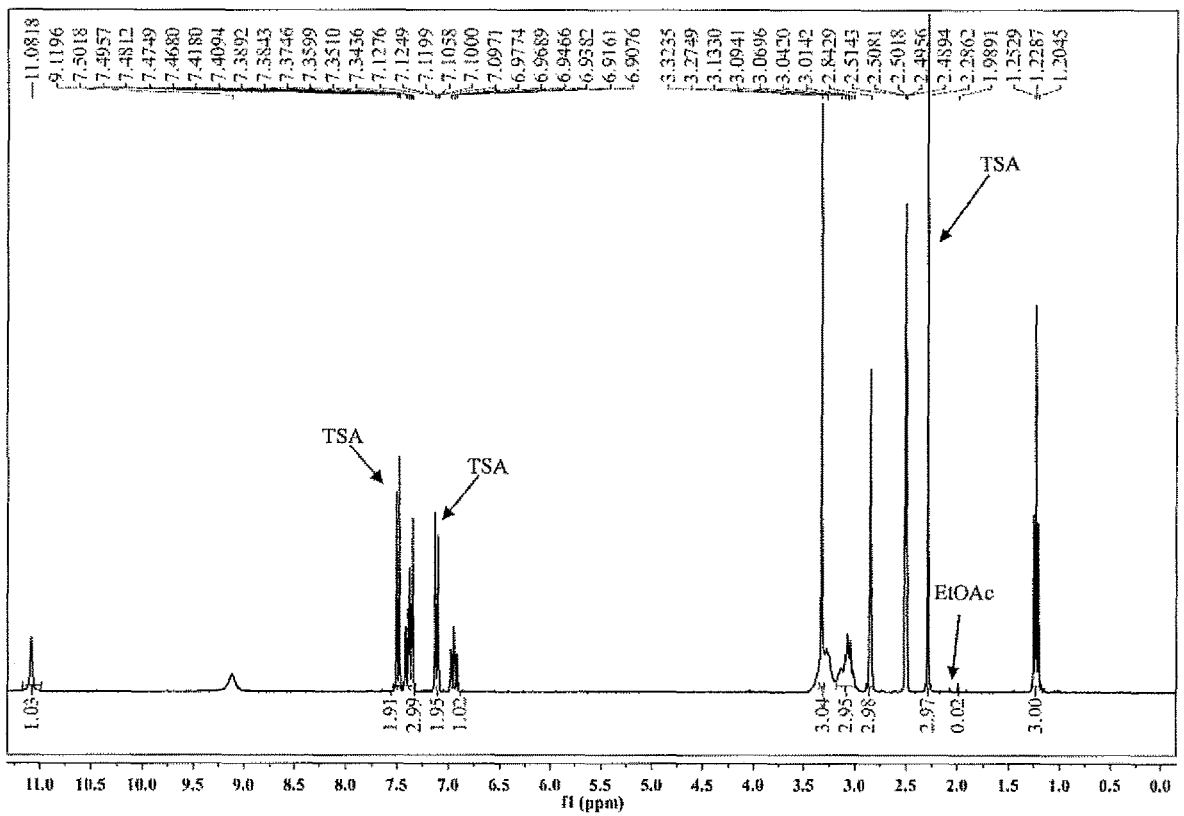
FIG. 5 depicts an $^1$H NMR spectrum (300 MHz, DMSO-d6) of N-ethyl-2-(5-fluoro-1H-indol-3-yl)-N-methylethan-1-amine p-tosylate.

In an embodiment, the X-ray powder diffraction pattern which was measured using Cu K-alpha radiation comprises peaks at 17.57±0.50 degrees, 18.77±0.50 degrees, and 23.59±0.50 degrees 2θ. In another embodiment, the X-ray powder diffraction pattern which was measured using Cu K-alpha radiation comprises peaks at 10.09±0.50 degrees, 14.85±0.50 degrees, 17.57±0.50 degrees, 18.77±0.50 degrees, and 23.59±0.50 degrees 2θ. In a further embodiment, the X-ray powder diffraction pattern which was measured using Cu K-alpha radiation comprises peaks at 10.09±0.50 degrees, 11.81±0.50 degrees, 14.85±0.50 degrees, 17.57±0.50 degrees, 18.77±0.50 degrees, 19.27±0.50 degrees, 22.32±0.50 degrees and 23.59±0.50 degrees 2θ. In an embodiment, the X-ray powder diffraction pattern which was measured using Cu K-alpha radiation comprises peaks at 2θ angles of 7.44±0.50, 10.99±0.50, 11.52±0.50, 11.81±0.50, 11.96±0.50, 12.11±0.50, 13.70±0.50, 14.56±0.50, 14.85±0.50, 15.81±0.50, 16.03±0.50, 17.17±0.50, 17.57±0.50, 18.16±0.50, 18.77±0.50, 19.27±0.50, 20.19±0.50, 20.48±0.50, 21.07±0.50, 21.73±0.50, 22.06±0.50, 22.32±0.50, 22.77±0.50, 23.11±0.50, 23.41±0.50, 23.59±0.50, 23.98±0.50, 24.25±0.50, 25.10±0.50, 25.59±0.50, 26.33±0.50, 26.47±0.50, 27.77±0.50, 28.52±0.50, 29.27±0.50, 29.56±0.50, 29.78±0.50, 31.39±0.50, 31.59±0.50, 32.04±0.50, 34.62±0.50, 34.92±0.50, 35.09±0.50, 35.31±0.50, 35.74±0.50, 36.27±0.50, 36.48, ±0.50, 36.92, ±0.50 37.61±0.50, 37.99±0.50, 38.26±0.50, 39.67±0.50 degrees 2θ. An $^1$H NMR spectrum of the p-tosylate product was also recorded according to the parameters described hereinabove, with the result depicted in FIG. 5.

Figure 6:
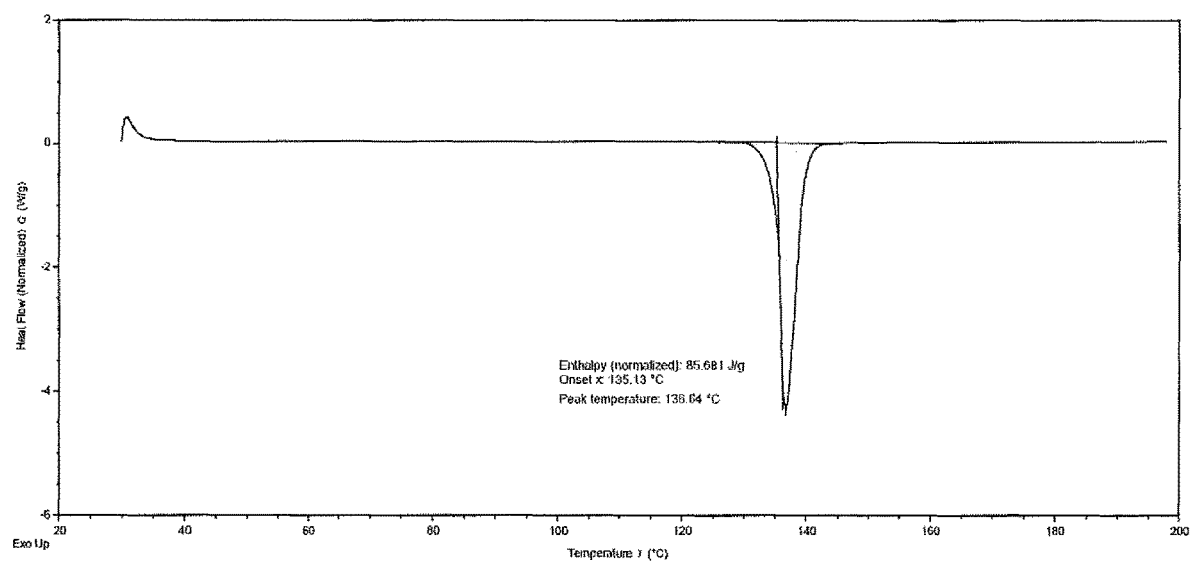
FIG. 6 depicts a DSC thermogram of N-ethyl-2-(5-fluoro-1H-indol-3-yl)-N-methylethan-1-amine p-tosylate.

A DSC thermogram of the p-tosylate product was collected according to the parameters described hereinabove, with the result depicted in FIG. 6. The DSC thermogram had a sharp temperature peak at about 137° C.

C. N-ethyl-2-(5-fluoro-1H-indol-3-yl)-N-methyl-ethan-1-amine hemimalate

N-ethyl-2-(5-fluoro-1H-indol-3-yl)-N-methylethan-1-amine hemimalate is prepared by reacting N-ethyl-2-(5-fluoro-1H-indol-3-yl)-N-methylethan-1-amine with L-malic acid under conditions effective to form N-ethyl-2-(5-fluoro-1H-indol-3-yl)-N-methylethan-1-amine hemimalate. For example, its preparation is conducted in a polar solvent, such as isopropyl alcohol. The reaction is conducted under effective conditions. For example, the reaction is heated slightly with stirring, at effective temperatures to form N-ethyl-2-(5-fluoro-1H-indol-3-yl)-N-methylethan-1-amine hemimalate and keep it fully or partially dissolved. For example, the reaction may be heated at a temperature ranging from about 30° C. to about 60° C., such as about 45° C., with stirring to form an oil and/or a gum comprising N-ethyl-2-(5-fluoro-1H-indol-3-yl)-N-methylethan-1-amine hemimalate. The oil and/or a gum comprising N-ethyl-2-(5-fluoro-1H-indol-3-yl)-N-methylethan-1-amine hemimalate may optionally be sonicated. It is cooled to about room temperature and the N-ethyl-2-(5-fluoro-1H-indol-3-yl)-N-methylethan-1-amine hemimalate is crystallized from the oil and/or gum, for example, by seeding, scratching, or aging, to form a crystalline solid substantially comprising N-ethyl-2-(5-fluoro-1H-indol-3-yl)-N-methylethan-1-amine hemimalate.

Although the procedure described the use of L-malic acid as the acid that reacts with N-ethyl-2-(5-fluoro-1H-indol-3-yl)-N-methylethan-1-amine, it is also applicable to reaction of N-ethyl-2-(5-fluoro-1H-indol-3-yl)-N-methylethan-1-amine with D-malic acid and to the racemic malic acid.

The following example is further illustrative of the subject matter in the present disclosure using L-malic acid as the representative malic acid that reacts with N-ethyl-2-(5-fluoro-1H-indol-3-yl)-N-methylethan-1-amine:

EXAMPLE 3: Preparation of N-ethyl-2-(5-fluoro-1H-indol-3-yl)-N-methylethan-1-amine hemimalate A mole equivalent of freebase was reacted with 0.55 equivalent of L-malic acid in 10 volumes of isopropyl alcohol. The mixture was stirred at 45° C. for 1 hour, cooled back to room temperature, and was allowed to stir for 3 days. The resultant slurry was filtered and the filter cake was washed with isopropyl alcohol to produce a while solid. The resulting white solid was dried overnight under vacuum. Crystalline N-ethyl-2-(5-fluoro-1H-indol-3-yl)-N-methyl-ethan-1-amine hemimalate was recovered and analyzed by XRPD according to the parameters described hereinabove. The XRPD diffractogram of N-ethyl-2-(5-fluoro-1H-indol-3-yl)-N-methylethan-1-amine hemimalate is depicted in FIG. 7. The peak values and intensity of the XPRD are provided hereinbelow in the following table:

| Angle (°2θ) | d-spacing (Å) | Relative intensity |
|---|---|---|
| 5.70 | 15.49 | 44 |
| 9.80 | 9.01 | 1 |
| 10.87 | 8.13 | 22 |
| 11.39 | 7.76 | 91 |
| 11.92 | 7.42 | 6 |
| 12.62 | 7.01 | 12 |
| 15.21 | 5.82 | 100 |
| 16.31 | 5.43 | 7 |
| 17.11 | 5.18 | 63 |
| 18.22 | 4.87 | 61 |
| 18.46 | 4.80 | 39 |
| 18.78 | 4.72 | 27 |
| 19.57 | 4.53 | 52 |
| 19.64 | 4.52 | 44 |
| 21.12 | 4.20 | 3 |
| 21.62 | 4.11 | 5 |
| 22.18 | 4.01 | 76 |
| 22.94 | 3.87 | 47 |
| 23.35 | 3.81 | 5 |
| 23.94 | 3.71 | 5 |
| 24.19 | 3.68 | 36 |
| 24.74 | 3.60 | 19 |
| 25.36 | 3.51 | 15 |
| 25.89 | 3.44 | 2 |
| 26.50 | 3.36 | 12 |
| 26.81 | 3.32 | 3 |
| 27.45 | 3.25 | 2 |
| 28.31 | 3.15 | 2 |
| 28.93 | 3.08 | 9 |
| 29.55 | 3.02 | 3 |
| 30.07 | 2.97 | 1 |
| 30.75 | 2.90 | 2 |
| 31.60 | 2.83 | 2 |
| 31.93 | 2.80 | 3 |
| 32.97 | 2.71 | 6 |
| 33.86 | 2.65 | 2 |
| 34.57 | 2.59 | 2 |
| 35.13 | 2.55 | 3 |
| 35.32 | 2.54 | 4 |
| 36.20 | 2.48 | 1 |
| 38.09 | 2.36 | 1 |
| 38.45 | 2.34 | 2 |
| 38.91 | 2.31 | 3 |
| 39.67 | 2.27 | 2 |

Note. Cut-off for relative intensity was 1.

As shown, in an embodiment, the X-ray powder diffraction pattern comprises peaks at 11.39±0.50 degrees, 15.21±0.50 degrees, and 22.18±0.50 degrees 2θ. In another embodiment, the X-ray powder diffraction pattern comprises peaks 11.39±0.50 degrees, 15.21±0.50 degrees, 17.11±0.50 degrees, 18.22±0.50 degrees, and 22.18±0.50 degrees 2θ. In a further embodiment, the X-ray powder diffraction pattern comprises peaks at 5.70±0.50 degrees, 11.39±0.50 degrees, 15.21±0.50 degrees, 17.11±0.50 degrees, 18.22±0.50 degrees, 18.46±0.50 degrees, 19.57±0.50 degrees, 19.64±0.50 degrees, 22.18±0.50 degrees, and 22.94±0.50 degrees 2θ. In a further embodiment, the X-ray powder diffraction pattern comprises peaks at 5.70±0.50, 9.80±0.50, 10.87±0.50, 11.39±0.50, 11.92±0.50, 12.62±0.50, 15.21±0.50, 16.31±0.50, 17.11±0.50, 18.22±0.50, 18.46±0.50, 18.78±0.50, 19.57±0.50, 19.64±0.50, 21.12±0.50, 21.62±0.50, 22.18±0.50, 22.94±0.50, 23.35±0.50, 23.94±0.50, 24.19±0.50, 24.74±0.50, 25.36±0.50, 25.89±0.50, 26.50±0.50, 26.81±0.50, 27.45±0.50, 28.31±0.50, 28.93±0.50, 29.55±0.50, 30.07±0.50, 30.75±0.50, 31.60±0.50, 31.93±0.50, 32.97±0.50, 33.86±0.50, 34.57±0.50, 35.13±0.50, 35.32±0.50, 36.20±0.50, 38.09±0.50, 38.45±0.50, 38.91±0.50, and 39.67±0.50 degrees 2θ.

Figure 8:
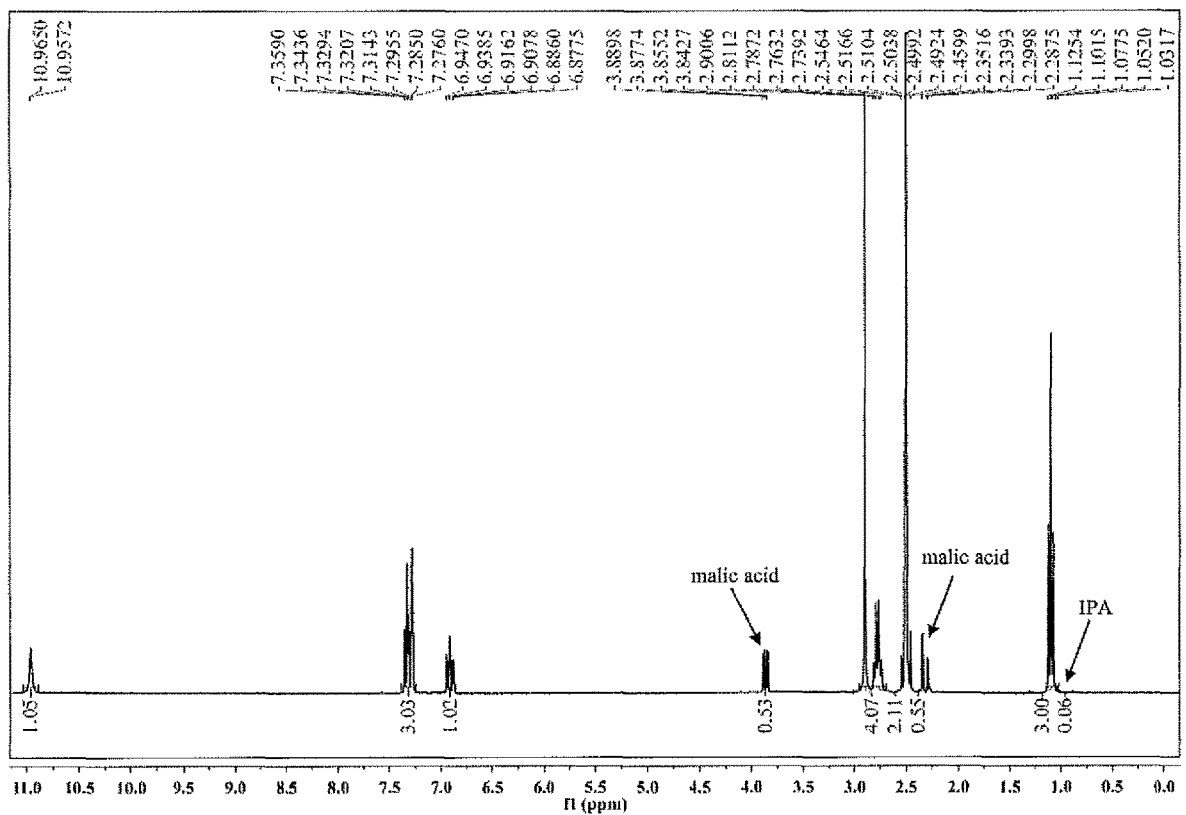
FIG. 8 depicts an $^1$H NMR spectrum (300 MHz, DMSO-d6) of N-ethyl-2-(5-fluoro-1H-indol-3-yl)-N-methylethan-1-amine hemimalate.

An $^1$H NMR of the hemimalate product was also recorded according to the parameters described hereinabove, with the result depicted in FIG. 8.

Figure 9:
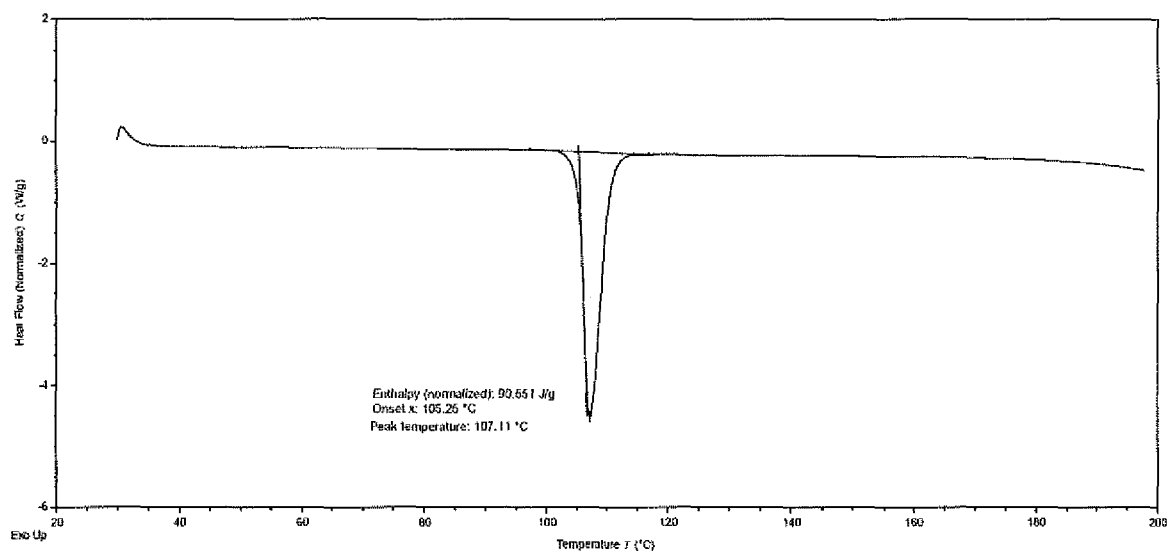
FIG. 9 depicts a DSC thermogram of N-ethyl-2-(5-fluoro-1H-indol-3-yl)-N-methylethan-1-amine hemimalate.

A DSC thermogram of the hemimalate was collected according to the parameters described hereinabove, with the result depicted in FIG. 9. A sharp peak temperature at about 107° C. was observed.

D. N-ethyl-2-(5-fluoro-1H-indol-3-yl)-N-methylethan-1-amine monosuccinate

N-ethyl-2-(5-fluoro-1H-indol-3-yl)-N-methylethan-1-amine monosuccinate is prepared by reacting N-ethyl-2-(5-fluoro-1H-indol-3-yl)-N-methylethan-1-amine with succinic acid under conditions effective to form N-ethyl-2-(5-fluoro-1H-indol-3-yl)-N-methylethan-1-amine monosuccinate. For example, its preparation is conducted in a polar solvent, for instance, ethanol. For example, the reaction is heated slightly with stirring, at effective temperatures to form N-ethyl-2-(5-fluoro-1H-indol-3-yl)-N-methylethan-1-amine monosuccinate and keep it fully or partially dissolved. For instance, the reaction may be heated at a temperature ranging from about 30° C. to about 60° C., such as about 45° C., with stirring to form N-ethyl-2-(5-fluoro-1H-indol-3-yl)-N-methylethan-1-amine monosuccinate. The first polar solvent comprising ethanol is evaporated to dryness to form an oil comprising N-ethyl-2-(5-fluoro-1H-indol-3-yl)-N-methylethan-1-amine monosuccinate. A crystallizing solvent, such as isopropyl alcohol, is added to the oil at a temperature ranging from about 30° C. to about 60° C., such as 45° C., to form a gum upon cooling to room temperature. Additional crystallizing solvent, i.e., isopropyl alcohol, is added to form a slurry, from which N-ethyl-2-(5-fluoro-1H-indol-3-yl)-N-methylethan-1-amine monosuccinate is crystallized, for example, by seeding, scratching, or aging.

Alternatively, after the oil is formed from the evaporation of the ethanol, acetone is added to the oil at a temperature effective to solubilize the oil, ranging from about 30° C. to about 60° C., such as 45° C., and then the resulting mixture is cooled to room temperature. A non-polar antisolvent, such as n-heptane is added to the solution with stirring to form a slurry comprising N-ethyl-2-(5-fluoro-1H-indol-3-yl)-N-methylethan-1-amine monosuccinate, from which a crystalline solid comprising N-ethyl-2-(5-fluoro-1H-indol-3-yl)-N-methylethan-1-amine monosuccinate is crystallized, for example, by seeding, scratching, or aging. The solids are collected by filtration and dried under vacuum. N-ethyl-2-(5-fluoro-1H-indol-3-yl)-N-methylethan-1-amine monosuccinate is stable upon drying, however, it deliquesces after overnight humidity exposure at 30° C./90% relative humidity (RH).

EXAMPLE 4: Preparation of N-ethyl-2-(5-fluoro-1H-indol-3-yl)-N-methylethan-1-amine monosuccinate N-ethyl-2-(5-fluoro-1H-indol-3-yl)-N-methylethan-1-amine monosuccinate is isolated from isopropyl alcohol by the following steps.

A molar equivalent of N-ethyl-2-(5-fluoro-1H-indol-3-yl)-N-methylethan-1-amine free base was reacted with 1.1 molar eq. of succinic acid in 10 volumes of ethanol solvent. The vial was stirred at 45° C. for approximately 2 hours before the solution was allowed to evaporate to dryness at room temperature. The resulting yellow oil was placed under active vacuum at 50° C. for an additional 3 h to dry thoroughly.

About 2 volumes of acetone was added to the dried oil and the resulting mixture was stirred for 2 h at 45° C. and then cooled to RT and stirred overnight. To the clear solution, about 1.5 volumes of n-heptane was dropwise added. The contents of the vial are stirred overnight. A white slurry is observed the next day and the crystalline N-ethyl-2-(5-fluoro-1H-indol-3-yl)-N-methylethan-1-amine monosuccinate was collected by filtration. The product was analyzed by XRPD according to the parameters described hereinabove.

The XRPD diffractogram of N-ethyl-2-(5-fluoro-1H-indol-3-yl)-N-methylethan-1-amine monosuccinate is depicted in FIG. 10. The peak values and intensity of the XPRD are provided hereinbelow in the following table:

| Angle (°2θ) | d-spacing (Å) | Relative intensity |
|---|---|---|
| 8.70 | 10.16 | 9 |
| 12.87 | 6.87 | 2 |
| 14.00 | 6.32 | 21 |
| 15.57 | 5.69 | 2 |
| 16.96 | 5.22 | 78 |
| 17.38 | 5.10 | 41 |
| 17.91 | 4.95 | 5 |
| 18.23 | 4.86 | 34 |
| 19.90 | 4.46 | 74 |
| 20.61 | 4.31 | 22 |
| 21.01 | 4.22 | 53 |
| 21.37 | 4.16 | 100 |
| 22.13 | 4.01 | 37 |
| 23.06 | 3.85 | 100 |
| 23.70 | 3.75 | 28 |
| 24.05 | 3.70 | 3 |
| 24.73 | 3.60 | 2 |
| 25.62 | 3.47 | 19 |
| 25.98 | 3.43 | 19 |
| 26.45 | 3.37 | 26 |
| 27.65 | 3.22 | 3 |
| 28.24 | 3.16 | 14 |
| 28.56 | 3.12 | 33 |

Note. Cut-off for relative intensity was 2

In an embodiment, the X-ray powder diffraction pattern comprises peaks at 16.96±0.50 degrees, 19.90±0.50 degrees, 21.37±0.50 degrees, and 23.06±0.50 degrees 2θ. In another embodiment, the monosuccinate is characterized with peaks at 16.96±0.50 degrees, 19.90±0.50 degrees, 21.01±0.50 degrees, 21.37±0.50 degrees, and 23.06±0.50 degrees 2θ.. In another aspect, the X-ray diffraction pattern. comprises peaks at 16.96±0.50 degrees, 17.38±0.50 degrees, 18.23±0.50 degrees, 19.90±0.50 degrees, 21.01±0.50 degrees, 21.37±0.50 degrees, 22.13±0.50 degrees, 23.06±0.50 degrees, and 28.56±0.50 degrees 2θ. In another aspect, the XRPD comprises peaks at 8.70±0.50, 12.87±0.50, 14.00±0.50, 15.57±0.50, 16.96±0.50, 17.38±0.50, 17.91±0.50, 18.23±0.50, 19.90±0.50, 20.61±0.50, 21.01±0.50, 21.37±0.50, 22.13±0.50, 23.06±0.50, 23.70±0.50, 24.05±0.50, 24.73±0.50, 25.62±0.50, 25.98±0.50, 26.45±0.50, 27.65±0.50, 28.24±0.50, and 28.56±0.50 degrees 2θ.

Figure 11:
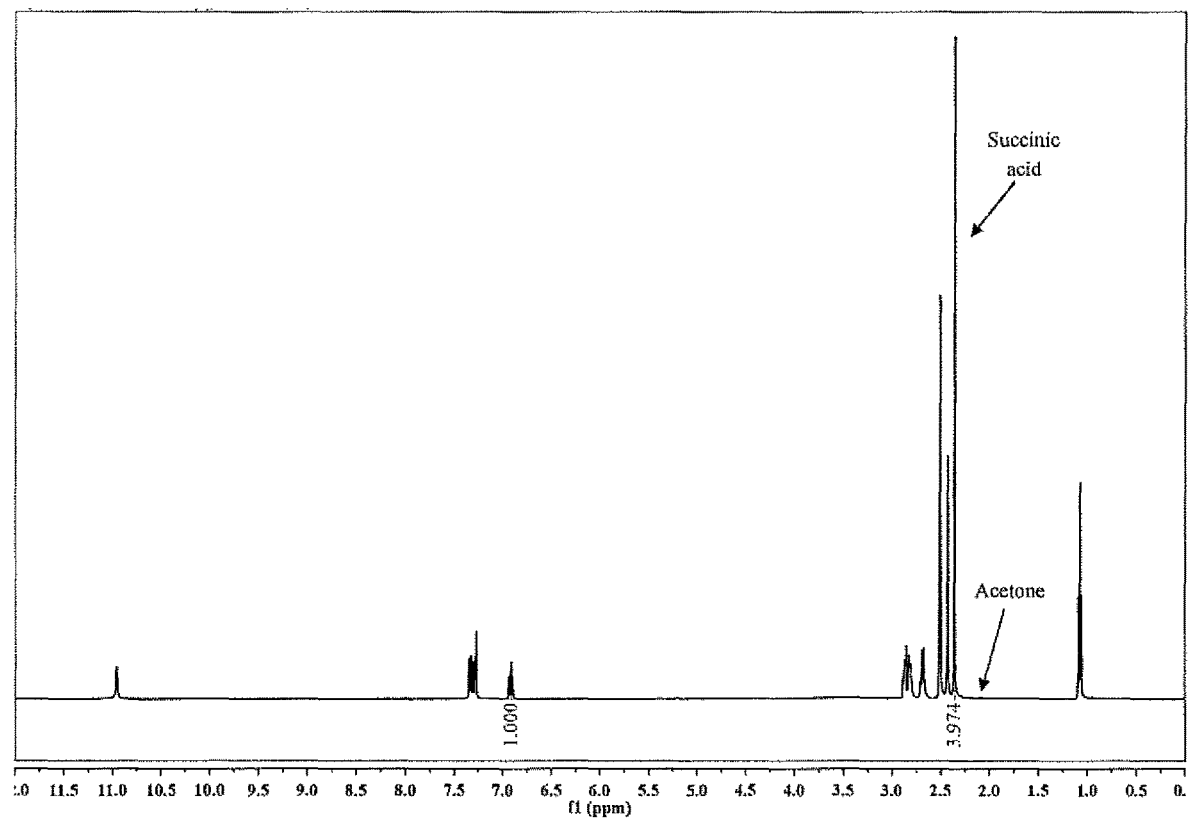
FIG. 11 depicts an $^1$H NMR spectra (300 MHz, DMSO d6) of N-ethyl-2-(5-fluoro-1H-indol-3-yl)-N-methylethan-1-amine monosuccinate

An $^1$H NMR spectrum of the monosuccinate product was also recorded, with the result depicted in FIG. 11.

Figure 12:
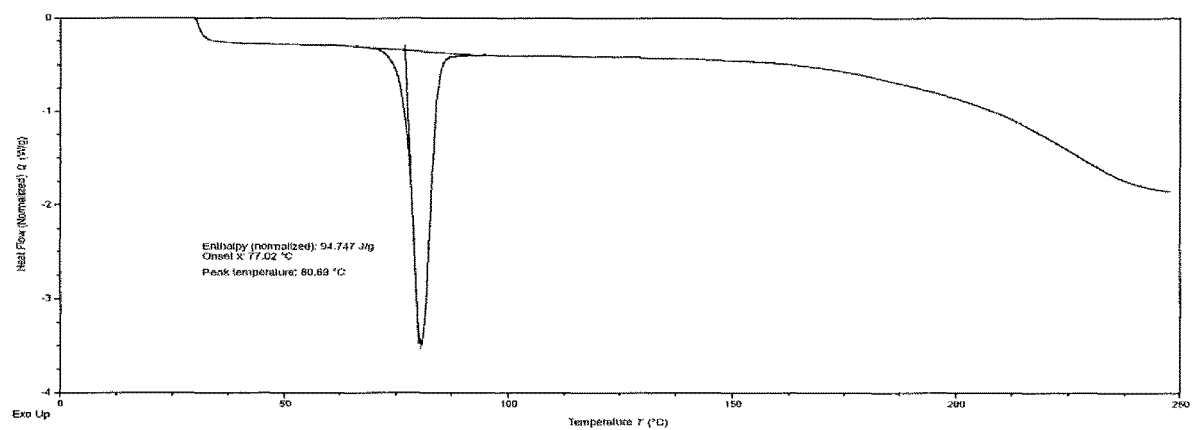
FIG. 12 depicts a DSC thermogram of N-ethyl-2-(5-fluoro-1H-indol-3-yl)-N-methylethan-1-amine monosuccinate.

A DSC thermogram of the monosuccinate product was recorded, with the result depicted in FIG. 12. The DSC thermogram showed one endotherm with a peak temperature of about 81° C.

E. Additional Data

Dynamic Vapor Sorption (DVS) was performed using a Q5000SA. The sample (5-15 mg) was loaded into a metallic quartz sample pan, suspended from a microbalance, and exposed to a humidified stream of nitrogen gas. Weight changes were relative to a matching empty reference pan opposite the sample, suspended from the microbalance. The sample was held for a minimum of 10 min at each level and only progressed to the next humidity level if there was <0.002% change in weight between measurements (interval: 5 s) or 45 min had elapsed (for 5-65% RH) or 2 h had elapsed (for 80 and 95% RH). The following programs were used:
1—Equilibration at 50% RH
2—50% to 5%. (50%, 35%, 20%, and 5%)
3—5% to 95% (5%, 20%, 35%, 50%, 65%, 80%, and 95%)
4—95% to 5% (95%, 80%, 65%, 50%, 35%, 20%, and 5%)
5—5% to 50% (5%, 20%, 35%, and 50%)
1—Equilibration at 50% RH
2—50% to 2%. (50%, 40%, 30%, 20%, 10%, and 2%)
3—2% to 75% (2%, 10%, 20%, 30%, 40%, 50%, 60%, 70% and 75%)
4—75% to 2% (75%, 70%, 60%, 50%, 40%, 30%, 20%, 10% and 2%)
5—2% to 50%(2%, 10%, 20%, 30%, 40% and 50%)

Figure 13:
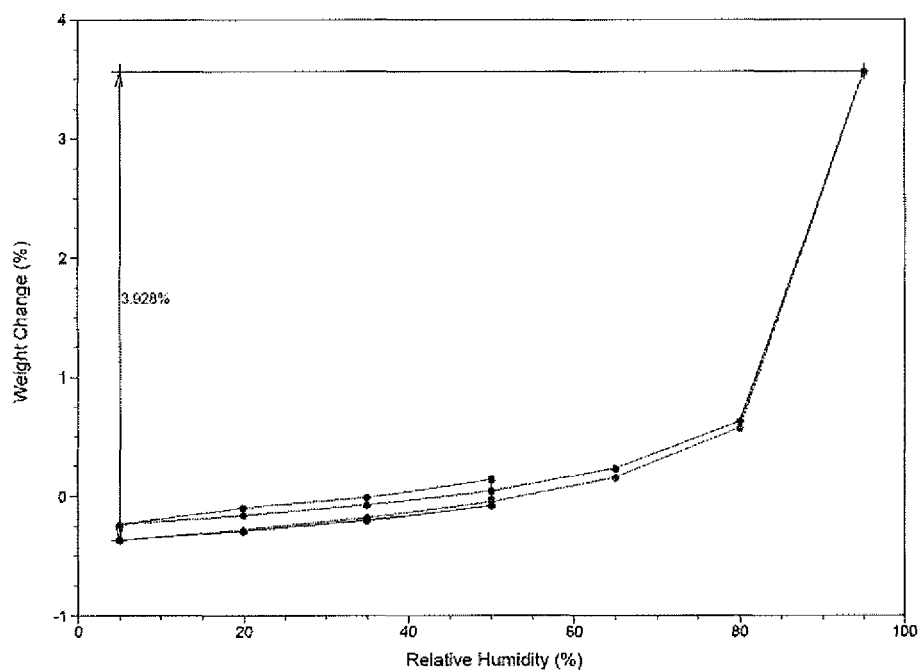
FIG. 13 graphically depicts the DVS isotherm plot of N-ethyl-2-(5-fluoro-1H-indol-3-yl)-N-methylethan-1-amine monophosphate.

The DVS isotherm plot of N-ethyl-2-(5-fluoro-1H-indol-3-yl)-N-methylethan-1-amine monophosphate is graphically depicted in FIG. 13.

Figure 14:
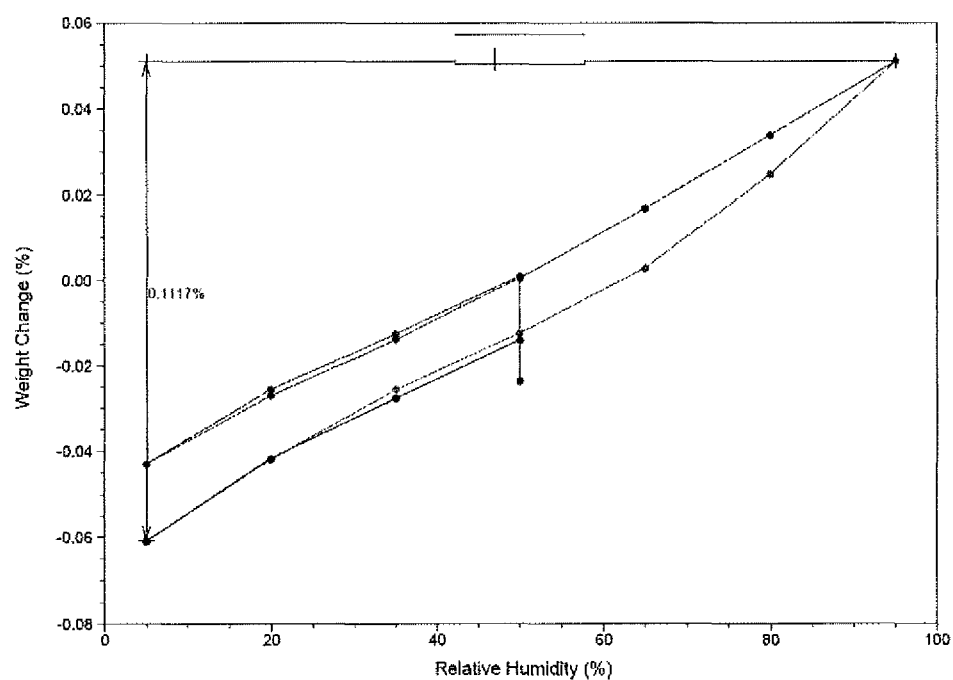
FIG. 14 graphically depicts the DVS isotherm plot of N-ethyl-2-(5-fluoro-1H-indol-3-yl)-N-methylethan-1-amine p-tosylate.

The DVS isotherm plot of N-ethyl-2-(5-fluoro-1H-indol-3-yl)-N-methylethan-1-amine p-tosylate is graphically depicted in FIG. 14.

Figure 15:
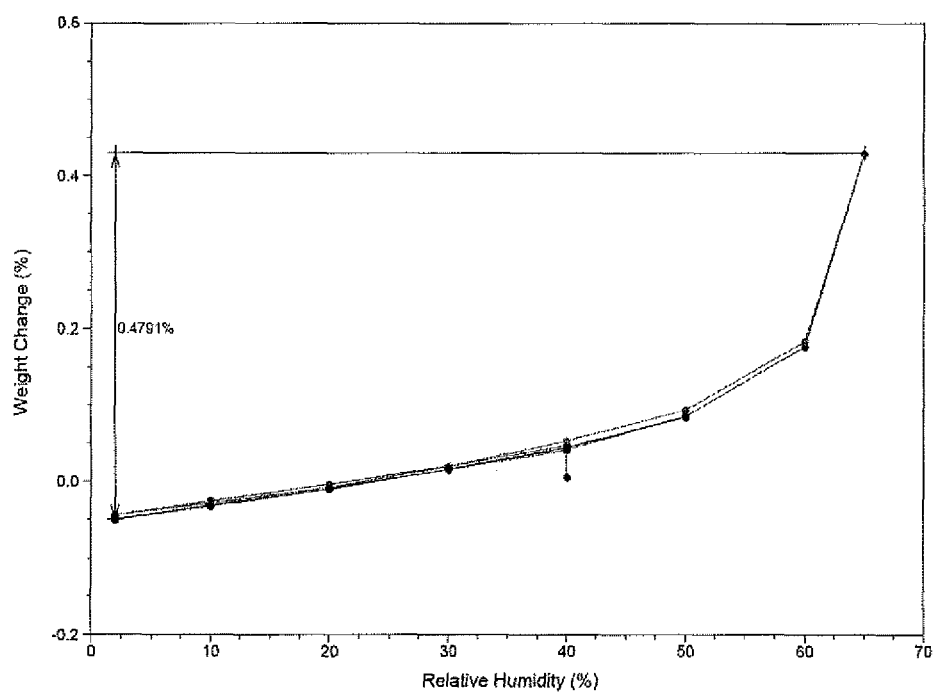
FIG. 15 graphically depicts the DVS isotherm plot of N-ethyl-2-(5-fluoro-1H-indol-3-yl)-N-methylethan-1-amine hemimalate.

With respect to N-ethyl-2-(5-fluoro-1H-indol-3-yl)-N-methylethan-1-amine hemimalate, the DVS isotherm plot is graphically depicted in FIG. 15.

F. Methods and Compositions

Also described herein are methods and compositions for treating a mood disorder by administering to a patient in need thereof a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein. Also provided are pharmaceutical compositions that include a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein.

In embodiments, the methods and compositions may be used to treat a mood disorder including depressive disorders, e.g., major depressive disorder, persistent depressive disorder, postpartum depression, premenstrual dysphoric disorder, seasonal affective disorder, psychotic depression, disruptive mood dysregulation disorder, substance/medication-induced depressive disorder, and depressive disorder due to another medical condition.

In some embodiments, depression conditions include major depressive disorder and dysthymic disorder. In some embodiments, depression conditions develop under unique circumstances, including, but are not limited to, psychotic depression, postpartum depression, seasonal affective disorder (SAD), mood disorder, depressions caused by chronic medical conditions such as cancer or chronic pain, chemotherapy, chronic stress, post-traumatic stress disorders, and bipolar disorder (or manic depressive disorder). In some embodiments, depression conditions that are expected to be treated according to this aspect of the present disclosure include, but are not limited to, major depressive disorder, dysthymic disorder, psychotic depression, postpartum depression, premenstrual syndrome, premenstrual dysphoric disorder, seasonal affective disorder (SAD), anxiety, mood disorder, depressions caused by chronic medical conditions such as cancer or chronic pain, chemotherapy, chronic stress, post-traumatic stress disorders, and bipolar disorder (or manic depressive disorder).

Also provided herein are methods of treating refractory depression, e.g., patients suffering from a depressive disorder that does not, and/or has not, responded to adequate courses of at least one, or at least two, other antidepressant compounds or therapeutics. For example, provided herein is a method of treating depression in a treatment resistant patient, comprising a) optionally identifying the patient as treatment resistant and b) administering an effective dose of a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine mono-succinate, as disclosed herein. In some embodiments, refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. In some embodiments, a treatment resistant-patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs, other than the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein. In some embodiments, a treatment-resistant patient may also be identified as one who is unwilling or unable to tolerate the side effects of one or more standard pharmacological or non-pharmacological treatment.

In some embodiments, symptoms associated with depression include, but are not limited to, persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, or suicide attempts. In some embodiments, various symptoms associated with anxiety include fear, panic, heart palpitations, shortness of breath, fatigue, nausea, and headaches among others. In addition, patients suffering from any form of depression often experience anxiety. It is expected that the methods of the present condition can be used to treat anxiety or any of the symptoms thereof. In some embodiments, presence, severity, frequency, and duration of symptoms of depression vary on a case-to-case basis.

In embodiments, the methods and compositions may be used to treat a mood disorder including bipolar and related disorders, e.g., bipolar I disorder, bipolar II disorder, cyclothymic disorder, substance/medication-induced bipolar and related disorder, and bipolar and related disorder due to another medical condition.

In embodiments, the methods and compositions may be used to treat a mood disorder including substance-related disorders, e.g., preventing a substance use craving, diminishing a substance use craving, and/or facilitating substance use cessation or withdrawal. Substance use disorders involve abuse of psychoactive compounds such as alcohol, caffeine, *cannabis*, inhalants, opioids, sedatives, hypnotics, anxiolytics, stimulants, nicotine and tobacco. As used herein "substance" or "substances" are psychoactive compounds which can be addictive such as alcohol, caffeine, *cannabis*, hallucinogens, inhalants, opioids, sedatives, hypnotics, anxiolytics, stimulants, nicotine and tobacco. For example, the methods and compositions may be used to facilitate smoking cessation or cessation of opioid use.

In embodiments, the methods and compositions may be used to treat a mood disorder including anxiety disorders, e.g., separation anxiety disorder, selective mutism, specific phobia, social anxiety disorder (social phobia), panic disorder, panic attack, agoraphobia, generalized anxiety disorder, substance/medication-induced anxiety disorder, and anxiety disorder due to another medical condition.

In embodiments, the methods and compositions may be used to treat a mood disorder including obsessive-compulsive and related disorders, e.g., obsessive-compulsive disorder, body dysmorphic disorder, hoarding disorder, trichotillomania (hair-pulling disorder), excoriation (skin-picking) disorder, substance/medication-induced obsessive-compulsive and related disorder, and obsessive-compulsive and related disorder due to another medical condition.

In embodiments, the methods and compositions may be used to treat a mood disorder including trauma- and stressor-related disorders, e.g., reactive attachment disorder, disinhibited social engagement disorder, posttraumatic stress disorder, acute stress disorder, and adjustment disorders.

In embodiments, the methods and compositions may be used to treat a mood disorder including feeding and eating disorders, e.g., anorexia nervosa, bulimia nervosa, binge-eating disorder, pica, rumination disorder, and avoidant/restrictive food intake disorder.

In embodiments, the methods and compositions may be used to treat a mood disorder including neurocognitive disorders, e.g., delirium, major neurocognitive disorder, mild neurocognitive disorder, major or mild neurocognitive disorder due to Alzheimer's disease, major or mild frontotemporal neurocognitive disorder, major or mild neurocognitive disorder with Lewy bodies, major or mild vascular neurocognitive disorder, major or mild neurocognitive disorder due to traumatic brain injury, substance/medication-induced major or mild neurocognitive disorder, major or mild neurocognitive disorder due to HIV infection, major or mild neurocognitive disorder due to prion disease, major or mild neurocognitive disorder due to Parkinson's disease, major or mild neurocognitive disorder due to Huntington's disease, major or mild neurocognitive disorder due to another medical condition, and major or mild neurocognitive disorder due to multiple etiologies.

In embodiments, the methods and compositions may be used to treat a mood disorder including neurodevelopmental disorders, e.g., autism spectrum disorder, attention-deficit/hyperactivity disorder, stereotypic movement disorder, tic disorders, Tourette's disorder, persistent (chronic) motor or vocal tic disorder, and provisional tic disorder. In some embodiments, a variety of other neurological conditions are expected to be treated according to the methods of the present disclosure. In some embodiments, neurological conditions include, but are not limited to, a learning disorder, autistic disorder, attention-deficit hyperactivity disorder, Tourette's syndrome, phobia, post-traumatic stress disorder, dementia, AIDS dementia, Alzheimer's disease, Parkinson's disease, spasticity, myoclonus, muscle spasm, bipolar disorder, a substance abuse disorder, urinary incontinence, and schizophrenia.

In embodiments, the methods and compositions may be used to treat a mood disorder including personality disorders, e.g., borderline personality disorder.

In embodiments, the methods and compositions may be used to treat a mood disorder including sexual dysfunctions, e.g., delayed ejaculation, erectile disorder, female orgasmic disorder, female sexual interest/arousal disorder, genito-pelvic pain/penetration disorder, male hypoactive sexual desire disorder, premature (early) ejaculation, and substance/medication-induced sexual dysfunction.

In embodiments, the methods and compositions may be used to treat a mood disorder including gender dysphoria.

In embodiments provided are methods and compositions for treating a mood disorder by administering to a subject in need thereof an effective amount of a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine mono-succinate, as described herein.

In other embodiments, provided herein are methods and compositions for treating migraine, cluster headache, or other headache disorders by administering to a patient in need thereof a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein.

In other embodiments, provided herein are methods and compositions for treating inflammation by administering to a patient in need thereof a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemi-malate, and N-ethyl-2-(5-fluoro-1H-indol-3-yl)-N-methylethan-1-amine monosuccinate, as disclosed herein.

In embodiments, methods include treating a mood disorder, e.g., a depressive disorder, by administering to a patient in need thereof a pharmaceutical composition including about 0.01 mg to about 400 mg of a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein. In embodiments, doses may be, e.g., in the range of about 0.01 to 400 mg, 0.01 to 300 mg, 0.01 to 250 mg, 0.01 to 200 mg, 0.01 to 150 mg, 0.01 to 100 mg, 0.01 to 75 mg, 0.01 to 50 mg, 0.01 to 25 mg, 0.01 to 20 mg, 0.01 to 15 mg, 0.01 to 10 mg, 0.01 to 5 mg, 0.01 to 1 mg, 0.01 to 0.5 mg, 0.01 to 0.1 mg, 0.1 to 300 mg, 0.1 to 250 mg, 0.1 to 200 mg, 0.1 to 150 mg, 0.1 to 100 mg, 0.1 to 75 mg, 0.1 to 50 mg, 0.1 to 25 mg, 0.1 to 20 mg, 0.1 to 15 mg, 0.1 to 10 mg, 0.1 to 5 mg, 0.1 to 1 mg, 10 to 300 mg, 10 to 250 mg, 10 to 200 mg, 10 to 150 mg, 10 to 100 mg, 10 to 50 mg, 10 to 25 mg, 10 to 15 mg, 20 to 300 mg, 20 to 250 mg, 20 to 200 mg, 20 to 150 mg, 20 to 100 mg, 20 to 50 mg, 50 to 300 mg, 50 to 250 mg, 50 to 200 mg, 50 to 150 mg, 50 to 100 mg, 100 to 300 mg, 100 to 250 mg, 100 to 200 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, and 400 mg being examples.

In specific embodiments, the dosages administered to a patient may include amounts of a crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine mono-succinate, as disclosed herein, in the range of about, e.g., 1 mg to 200 mg, 1 mg to 100 mg, 1 mg to 50 mg, 1 mg to 40 mg, 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.0 mg, 1.5 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 15 mg, 20 mg, 25 mg, 30 mg, 35 mg, 40 mg, 45 mg, 50 mg, 60 mg, 75 mg, 80 mg, 90 mg, 100 mg, 125 mg, 150 mg, and 200 mg being specific examples of doses.

Typically, dosages of the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, are administered once, twice, three or four times daily, every other day, every three days, once weekly, twice monthly, once monthly, or 3-4 times yearly to a patient in need thereof. In embodiments, the dosage is about, e.g., 1-400 mg/day, or 1-300 mg/day, or 1-250 mg/day, or 1-200 mg/day, for example 300 mg/day, 250 mg/day, 200 mg/day, 150 mg/day, 100 mg/day, 75 mg/day, 50 mg/day, 40 mg/day, 30 mg/day, 25 mg/day, 20 mg/day, 15 mg/day, 10 mg/day, 5 mg/day, or 1 mg/day.

In embodiments, pharmaceutical compositions for parenteral administration or inhalation, e.g., a spray or mist, of the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, include a concentration in a pharmaceutically acceptable liquid carrier of about 0.005 mg/ml to about 500 mg/mL. In embodiments, the compositions include the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, in a pharmaceutically acceptable liquid carrier at a concentration of, e.g., about 0.05 mg/mL to about 50 mg/mL, about 0.05 mg/mL to about 100 mg/mL, about 0.005 mg/mL to about 500 mg/mL, about 0.1 mg/mL to about 50 mg/mL, about 0.1 mg/mL to about 10 mg/mL, about 0.05 mg/mL to about 25 mg/mL, about 0.05 mg/mL to about 10 mg/mL, about 0.05 mg/mL to about 5 mg/mL, or about 0.05 mg/mL to about 1 mg/mL.

In embodiments, the composition includes the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, in a pharmaceutically acceptable liquid carrier at a concentration of, e.g., about 0.05 mg/mL to about 15 mg/mL, about 0.5 mg/mL to about 10 mg/mL, about 0.25 mg/mL to about 5 mg/mL, about 0.5 mg/mL to about 7 mg/mL, about 1 mg/mL to about 10 mg/mL, about 5 mg/mL to about 10 mg/mL, about 5 mg/mL to about 15 mg/mL, about 5 mg/mL to 25 mg/mL, about 5 mg/mL to 50 mg/mL, or about 10 mg/mL to 100 mg/mL. In embodiments, the pharmaceutical compositions are formulated as a total volume of about, e.g., 10 mL, 20 mL, 25 mL, 50 mL, 100 mL, 200 mL, 250 mL, or 500 mL.

For example, dosages may be administered to a subject once, twice, three or four times daily, every other day, every three days, once weekly, twice monthly, once monthly, or 3-4 times yearly. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine mono-p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered in s pharmaceutical composition comprising to a subject once in the morning, or once in the evening. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject once in the morning, and once in the evening. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject three times a day (e.g., at breakfast, lunch, and dinner), at a dose, e.g., of 50 mg/administration (e.g., 150 mg/day).

In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 12.5 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 25 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 35 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 50 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 75 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 100 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 150 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 200 mg/day in one or more doses. In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a subject in a pharmaceutical composition at 250 mg/day in one or more doses.

In embodiments, the dosage of the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is 0.0005-5 mg/kg, 0.001-1 mg/kg, 0.01-1 mg/kg or 0.1-5 mg/kg once, twice, three times or four times daily. For example, in embodiments, the dosage is 0.0005 mg/kg, 0.001 mg/kg, 0.005 mg/kg, 0.01 mg/kg, 0.025 mg/kg, 0.05 mg/kg, 0.1 mg/kg, 0.15 mg/kg, 0.2 mg/kg, 0.25 mg/kg, 0.3 mg/kg, 0.4 mg/kg, 0.5 mg/kg, 0.75 mg/kg, 1 mg/kg, 2.5 mg/kg, or 5 mg/kg, once, twice, three times or four times daily. In embodiments, a subject is administered a total daily dose of 0.01 mg to 500 mg of the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, once, twice, three times, or four times daily. In embodiments, the total amount administered to a subject in a 24-hour period is, e.g., 0.01 mg, 0.025 mg, 0.05 mg, 0.075 mg, 0.1 mg, 0.125 mg, 0.15 mg, 0.175 mg, 0.2 mg, 0.25 mg, 0.3 mg, 0.4 mg, 0.5 mg, 0.75 mg, 1 mg, 1.5 mg, 2 mg, 2.5 mg, 3 mg, 4 mg, 5 mg, 7.5 mg, 10 mg, 12.5 mg, 15 mg, 17.5 mg, 20 mg, 25 mg, 30 mg, 35 mg, 40 mg, 45 mg, 50 mg, 60 mg, 75 mg, 80 mg, 90 mg, 100 mg, 125 mg, 150 mg, 175 mg, 200 mg, 250 mg, 300 mg, 400 mg, or 500 mg. In embodiments, the subject may be started at a low dose and the dosage is escalated. In embodiments, the subject may be started at a high dose and the dosage is decreased.

In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, may be administered, e.g., via inhalation or orally, at specified intervals. For example, during treatment a patient may be administered in a pharmaceutical composition the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, at intervals of every, e.g., 1 year, 6 months, 90 days, 60 days, 30 days, 14 days, 7 days, 3 days, 24 hours, 12 hours, 8 hours, 6 hours, 5 hours, 4 hours, 3 hours, 2.5 hours, 2.25 hours, 2 hours, 1.75 hours, 1.5 hours, 1.25 hours, 1 hour, 0.75 hour, 0.5 hour, or 0.25 hour.

In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered to a patient in a pharmaceutical composition under the supervision of a healthcare provider.

In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered in a pharmaceutical composition to a patient under the supervision of a healthcare provider at a clinic specializing in the delivery of psychoactive treatments.

In embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered in a pharmaceutical composition to a patient under the supervision of a healthcare provider at a high dose intended to induce a psychedelic experience in the subject, e.g., 10 mg, 12.5 mg, 15 mg, 17.5 mg, 20 mg, 25 mg, 30 mg, 35 mg, 40 mg, 45 mg, 50 mg, 60 mg, 70 mg, 80 mg, 90 mg, 100 mg, 125 mg, or 150 mg.

In some embodiments, the administration to a patient of a high dose under the supervision of a healthcare provider occurs periodically in order to maintain a therapeutic effect in the patient, e.g., every three days, twice weekly, once weekly, twice monthly, once monthly, thrice yearly, twice yearly, or once yearly.

In some embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered by a patient on their own at home or otherwise away from the supervision of a healthcare provider.

In some embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, is administered by a patient on their own at home or otherwise away from the supervision of a healthcare provider at a low dose intended to be sub-perceptual or to induce threshold psychoactive effects, e.g., 0.1 mg, 0.25 mg, 0.5 mg, 0.75 mg, 1 mg, 1.5 mg, 2 mg, 2.5 mg, 3 mg, 4 mg, 5 mg, 7.5 mg, or 9 mg.

In some embodiments, the administration by a patient of a low dose on their own occurs periodically in order to maintain a therapeutic effect in the patient, e.g., daily, every other day, every three days, twice weekly, once weekly, twice monthly, or once monthly.

Suitable dosage forms for the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, include, but are not limited to, oral forms, such as tablets, hard or soft gelatin capsules, powders, granules and oral solutions, syrups or suspensions, troches, as well as sublingual, buccal, intratracheal, intraocular, or intranasal forms, forms adapted to inhalation, topical forms, transdermal forms, or parenteral forms, for example, forms adapted for intravenous, intra-arterial, intraperitoneal, intrathecal, intraventricular, intramuscular, or subcutaneous administration. In embodiments, for such parenteral administration, it may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The present disclosure further relates, in part, to pharmaceutical compositions comprising the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, in association with a pharmaceutical carrier, adjuvants and/or vehicles (together referred to as excipients). Pharmaceutical compositions herein may be provided with immediate release, delayed release, extended release, or modified release profiles. In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such compositions may be provided as pulsatile formulations, multilayer tablets, or capsules containing tablets, beads, granules, and the like. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, glidants, disintegrants, fillers, and coating compositions.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association the compounds described in the disclosure or combinations thereof with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents. Such auxiliary agents are suitably selected with respect to the intended form and route of administration and as consistent with conventional pharmaceutical practices.

Pharmaceutical compositions suitable for oral administration may be presented in solid dosage forms for oral administration as discrete dosage units such as pills, tablets, powders, granules, dragées or capsules, or as a powder or granules, or as a solution or suspension. The active ingredient comprising the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, may also be presented as a bolus or paste. The compositions can further be processed into a suppository or enema for rectal administration.

Tablets may contain the active ingredient, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, and suitable binders, lubricants, disintegrating agents, coloring agents, flavoring agents, flow-inducing agents, and melting agents. Gelatin capsules may contain the active ingredient, in any of the salt forms disclosed herein, and powdered carriers, such as lactose, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

For oral administration in liquid dosage form, the oral drug components are combined with any oral, non-toxic, pharmaceutically acceptable inert carrier such as ethanol, glycerol, water, and the like. Examples liquid dosage forms include, but are not limited to, solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Liquid dosage forms for oral administration can contain coloring and flavoring to increase patient acceptance.

For parenteral administration, suitable compositions include aqueous and non-aqueous sterile solutions. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration, e.g. by nasal inhalation, include fine dusts or mists which may be generated by means of metered dose pressurized aerosols, nebulizers or insufflators. Parenteral and intravenous forms may also include minerals and other materials to make them compatible with the type of injection or delivery system chosen.

The crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, used in the method of the present disclosure may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate may be administered as components of tissue-targeted emulsions.

The crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate used in the method of the present disclosure may also be coupled to soluble polymers as targetable drug carriers or as prodrugs. Such polymers include polyvinylpyrrolidone, pyran copolymer, polyhydroxylpropylmethacrylamide-phenol, polyhydroxyethylasparta-midephenol, or polyethylene-oxide-polylysine substituted with palmitoyl residues. Furthermore, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Pharmaceutical compositions herein may be provided with immediate release, delayed release, extended release, or modified release profiles. In some embodiments, pharmaceutical compositions with different drug release profiles may be combined to create a two-phase or three-phase release profile. For example, pharmaceutical compositions may be provided with an immediate release and an extended-release profile. In some embodiments, pharmaceutical compositions may be provided with an extended release and delayed release profile. Such composition may be provided as pulsatile formulations, multilayer tablets, or capsules containing tablets, beads, granules, and the like.

Pharmaceutical compositions herein may be provided with abuse deterrent features by techniques know in the art, for example, by making a tablet that is difficult to crush or to dissolve in water.

The disclosure further includes a pharmaceutical composition, as hereinbefore described, in combination with packaging material, including instructions for the use of the composition for a use as hereinbefore described.

The exact dose and regimen of administration of the composition will necessarily be dependent upon the type and magnitude of the therapeutic or nutritional effect to be achieved and may vary depending on factors such as the particular crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine mono p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, formula, route of administration, or age and condition of the individual subject to whom the composition is to be administered.

The crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine mono-p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate used in the method of the present disclosure may be administered in various forms, including those detailed herein. The treatment with the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate may be a component of a combination therapy or an adjunct therapy, i.e. the subject or patient in need of the drug is treated or given another drug for the disease in conjunction with one or more of the instant crystalline N-ethyl-2-(5-fluoro-1H-indol-3-yl)-N-methylethan-1-amine salts selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate. This combination therapy can be sequential therapy, where the patient is treated first with one drug and then the other, or the two drugs are given simultaneously. These can be administered independently by the same route or by two or more different routes of administration depending on the dosage forms employed.

In some embodiments, the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, may be administered in combination with one or more other antidepressant treatments, such as, tricyclic antidepressants, MAOIs, SSRIs, and double and triple uptake inhibitors and/or anxiolytic drugs for manufacturing a medicament for treating depression, anxiety, and/or other related diseases, including to provide relief from depression or anxiety and preventing recurrence of depression or anxiety. In some embodiments, therapeutics that may be used in combination with the crystalline N-ethyl-2-(5-fluoro-1H-indol-3-yl)-N-methylethan-1-amine salt selected from N-ethyl-2-(5-fluoro-1H-indol-3-yl)-N-methylethan-1-amine monophosphate, N-ethyl-2-(5-fluoro-1H-indol-3-yl)-N-methylethan-1-amine p-tosylate, N-ethyl-2-(5-fluoro-1H-indol-3-yl)-N-methylethan-1-amine hemimalate, and N-ethyl-2-(5-fluoro-1H-indol-3-yl)-N-methylethan-1-amine monosuccinate, as disclosed herein, include, but are not limited to, Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), Savella, Fetzima, Pristiq, and Ludiomill.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A crystalline salt of N-ethyl-2-(5-fluoro-1H-indol-3-yl)-N-methylethan-1-amine selected from crystalline N-ethyl-2-(5-fluoro-1H-indol-3-yl)-N-methylethan-1-amine monophosphate, crystalline N-ethyl-2-(5-fluoro-1H-indol-3-yl)-N-methylethan-1-amine p-tosylate, crystalline N-ethyl-2-(5-fluoro-1H-indol-3-yl)-N-methylethan-1-amine hemimalate, and crystalline N-ethyl-2-(5-fluoro-1H-indol-3-yl)-N-methylethan-1-amine monosuccinate.

2. The crystalline salt of claim 1, which is crystalline N-ethyl-2-(5-fluoro-1H-indol-3-yl)-N-methylethan-1-amine monophosphate.

3. The crystalline salt of claim 2 characterized by an X-ray powder diffraction pattern measured using Cu K-alpha radiation comprising peaks at 2θ angles of 10.99±0.50 degrees, 13.34±0.50 degrees, 15.92±0.50 degrees, 23.88±0.50 degrees, and 24.34±0.50 degrees.

4. The crystalline salt of claim 2 characterized by an X-ray powder diffraction pattern measured using Cu K-alpha radiation comprising peaks at 2θ angles of 10.99±0.50 degrees, 13.34±0.50 degrees, 15.92±0.50 degrees, 16.28±0.50 degrees, 19.24±0.50 degrees, 22.30±0.20 degrees, 23.38±0.50 degrees, 23.88±0.50 degrees, 24.34±0.50 degrees, and 27.22±0.50 degrees.

5. The crystalline salt of claim 2 characterized by an X-ray powder diffraction pattern measured using Cu K-alpha radiation substantially as depicted in FIG. 1.

6. The crystalline salt of claim 2 characterized by a DSC thermogram having at least one endotherm with a peak temperature of about 206° C.

Figure 3:
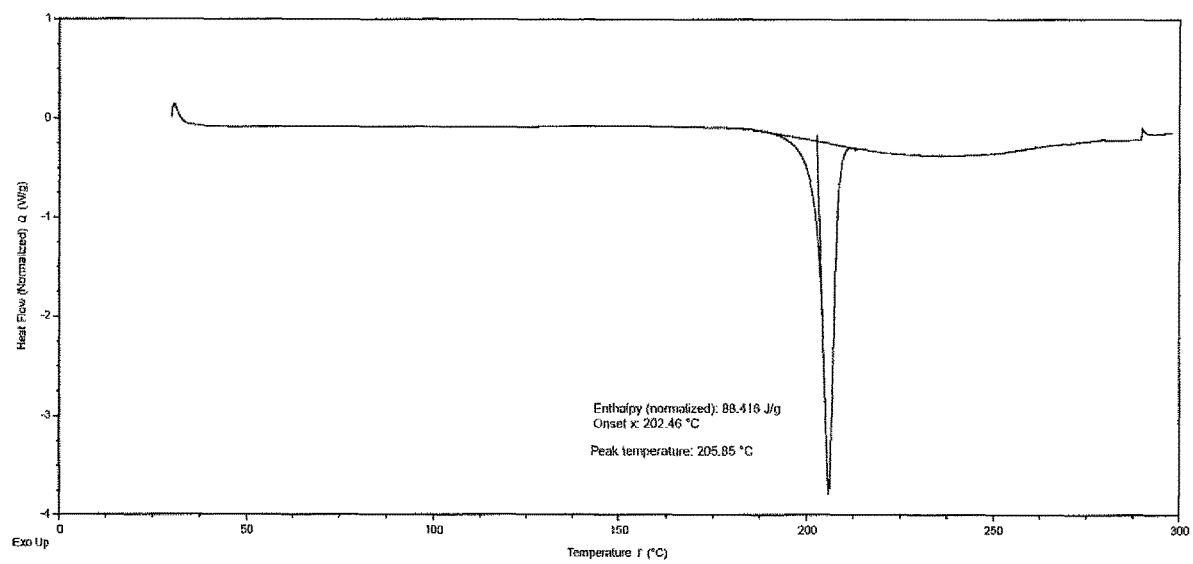
FIG. 3 depicts a DSC thermogram of N-ethyl-2-(5-fluoro-1H-indol-3-yl)-N-methylethan-1-amine monophosphate.

7. The crystalline salt of claim 2 characterized by a DSC thermogram substantially as depicted in FIG. 3.

8. The crystalline salt of claim 1, which is crystalline N-ethyl-2-(5-fluoro-1H-indol-3-yl)-N-methylethan-1-amine p-tosylate.

9. The crystalline salt of claim 8 characterized by an X-ray powder diffraction pattern measured using Cu K-alpha radiation comprising peaks at 2θ angles of 10.09±0.20 degrees, 14.85±0.50 degrees, 17.57±0.50 degrees, 18.77±0.50 degrees, and 23.59±0.50 degrees.

10. The crystalline salt of claim 8 characterized by an X-ray powder diffraction pattern measured using Cu K-alpha radiation comprising peaks at 2θ angles of 10.09±0.20 degrees, 11.81±0.50 degrees, 14.85±0.50 degrees, 17.57±0.50 degrees, 18.77±0.50 degrees, 19.27±0.50 degrees, 20.19±0.50 degrees, 20.48±0.50 degrees, 22.32±0.50 degrees, and 23.59±0.50 degrees.

11. The crystalline salt of claim 8 characterized by an X-ray powder diffraction pattern measured using Cu K-alpha radiation substantially as depicted in FIG. 4.

12. The crystalline salt of claim 8 characterized by a DSC thermogram having at least one endotherm with a peak temperature of about 137° C.

13. The crystalline salt of claim 8 characterized by a DSC thermogram substantially as depicted in FIG. 6.

14. The crystalline salt of claim 1, which is crystalline N-ethyl-2-(5-fluoro-1H-indol-3-yl)-N-methylethan-1-amine hemimalate.

15. The crystalline salt of claim 14 characterized by an X-ray powder diffraction pattern measured using Cu K-alpha radiation comprising peaks at 2θ angles of 11.39±0.50 degrees, 15.21±0.50 degrees, 17.11±0.50 degrees, 18.22±0.50 degrees, and 22.18±0.50 degrees.

16. The crystalline salt of claim 14 characterized by an X-ray powder diffraction pattern measured using Cu K-alpha radiation comprising peaks at 2θ angles of 5.70±0.50 degrees, 11.39±0.50 degrees, 15.21±0.50 degrees, 17.11±0.50 degrees, 18.22±0.50 degrees, 18.46±0.50 degrees, 19.57±0.50 degrees, 19.64±0.50 degrees, 22.18±0.50 degrees, and 22.94±0.50 degrees.

17. The crystalline salt of claim 14 characterized by an X-ray powder diffraction pattern measured using Cu K-alpha radiation substantially as depicted in FIG. 7.

18. The crystalline salt of claim 14 characterized by a DSC thermogram having at least one endotherm with a peak temperature of about 107° C.

19. The crystalline salt of claim 14 characterized by a DSC thermogram substantially as depicted in FIG. 9.

20. The crystalline salt of claim 1, which is crystalline N-ethyl-2-(5-fluoro-1H-indol-3-yl)-N-methylethan-1-amine monosuccinate.

21. The crystalline salt of claim 20 characterized by an X-ray powder diffraction pattern measured using Cu K-alpha radiation comprising peaks at 2θ angles of 16.96±0.50 degrees, 19.90±0.50 degrees, 21.01±0.50 degrees, 21.37±0.50 degrees, and 23.06±0.50 degrees.

22. The crystalline salt of claim 20 characterized by an X-ray powder diffraction pattern measured using Cu K-alpha radiation comprising peaks at 2θ angles of 16.96±0.50 degrees, 17.38±0.50 degrees, 18.23±0.50 degrees, 19.90±0.50 degrees, 21.01±0.50 degrees, 21.37±0.50 degrees, 22.13±0.50 degrees, 23.06±0.50 degrees, 23.70±0.50 degrees, and 28.56±±0.50 degrees.

23. The crystalline salt of claim 20 characterized by an X-ray powder diffraction pattern measured using Cu K-alpha radiation substantially as depicted in FIG. 10.

24. The crystalline salt of claim 20 characterized by a DSC thermogram having at least one endotherm with a peak temperature of about 81° C.

25. The crystalline salt of claim 20 characterized by a DSC thermogram substantially as depicted in FIG. 12.

26. A solid form of N-ethyl-2-(5-fluoro-1H-indol-3-yl)-N-methylethan-1-amine comprising any one or more of the crystalline N-ethyl-2-(5-fluoro-1H-indol-3-yl)-N-methylethan-1-amine salts of claim 1.

27. The solid form of claim 26 comprising at least 50% by weight of any one of the crystalline N-ethyl-2-(5-fluoro-1H-indol-3-yl)-N-methylethan-1-amine salts.

28. A pharmaceutical composition comprising any one or more of the crystalline salts of claim 1 and a pharmaceutically acceptable carrier therefor.

29. The pharmaceutical composition of claim 28 in solid dosage form.

30. A method of treating a mood disorder in a subject in need of such treatment comprising administering to said subject a therapeutically effective amount of the composition of claim 28.

* * * * *